United States Patent [19]
Anderson et al.

[11] Patent Number: 5,032,514
[45] Date of Patent: * Jul. 16, 1991

[54] METABOLIC PATHWAY ENGINEERING TO INCREASE PRODUCTION OF ASCORBIC ACID INTERMEDIATES

[75] Inventors: Stephen Anderson, San Mateo; Robert A. Lazarus, Millbrae; Harvey I. Miller, Pleasant Hill; R. Kevin Stafford, San Mateo, all of Calif.

[73] Assignee: Genentech, Inc., San Francisco, Calif.

[*] Notice: The portion of the term of this patent subsequent to Apr. 16, 2008 has been disclaimed.

[21] Appl. No.: 229,598

[22] Filed: Aug. 8, 1988

[51] Int. Cl.$^5$ .................. C12P 7/60; C12N 15/03
[52] U.S. Cl. .................. 435/138; 435/172.3
[58] Field of Search ............ 435/138, 172.3, 252.3, 435/823, 847

[56] References Cited

U.S. PATENT DOCUMENTS 2,917,435  12/1959  Perlman .................. 435/138
4,748,122   5/1988  Sonoyama et al. ......... 435/138
4,757,012   7/1988  Estell et al. ............ 435/138

FOREIGN PATENT DOCUMENTS 0276832  8/1988  European Pat. Off. ...... 435/138
000863   2/1987  World Int. Prop. O. ..... 435/138

OTHER PUBLICATIONS

Anderson et al., "Production of 2-keto-1-gulonate, An Intermediate in 1-Ascorbate Synthesis", by a Genetically Modified *Erlvinia herbicola*, Science, 230:144–149, 1985.

Primary Examiner—Douglas W. Robinson
Assistant Examiner—Marian C. Knode
Attorney, Agent, or Firm—Ginger R. Dreger

[57] ABSTRACT

In recombinant microorganisms which were rendered capable of converting 2,5-diketo-D-gluconic acid (2,5-DKG) to 2-keto-L-gulonic acid (2-KLG) by transfer of genetic material, the secondary metabolites and metabolic pathways leading to the metabolic diversion of 2-KLG and 2,5-DKG were determined, and the diversion of 2-KLG to L-iodonic acid (IA) or of 2,5-DKG to 5-keto-D-gluconate (5-KDH) was blocked.

12 Claims, 19 Drawing Sheets

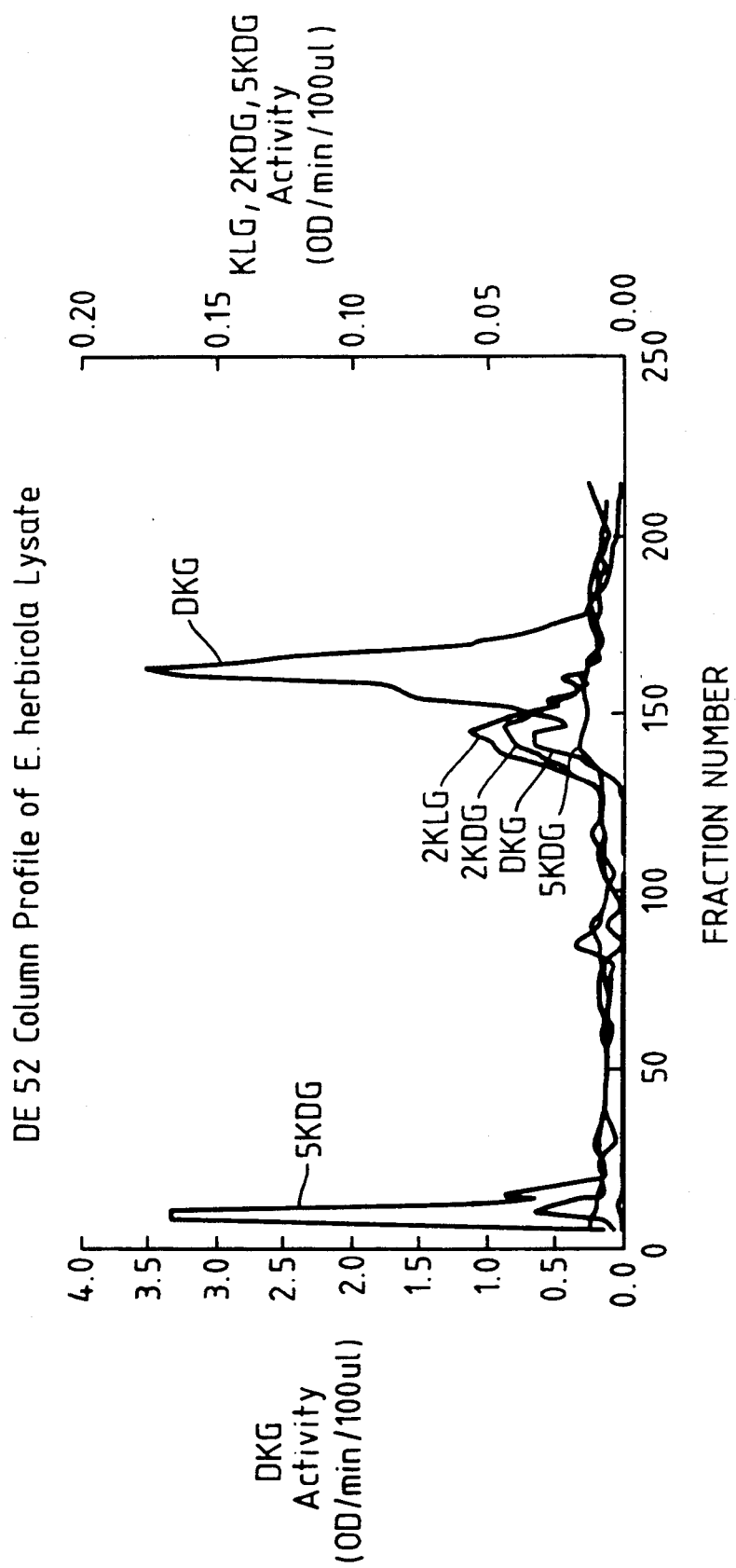

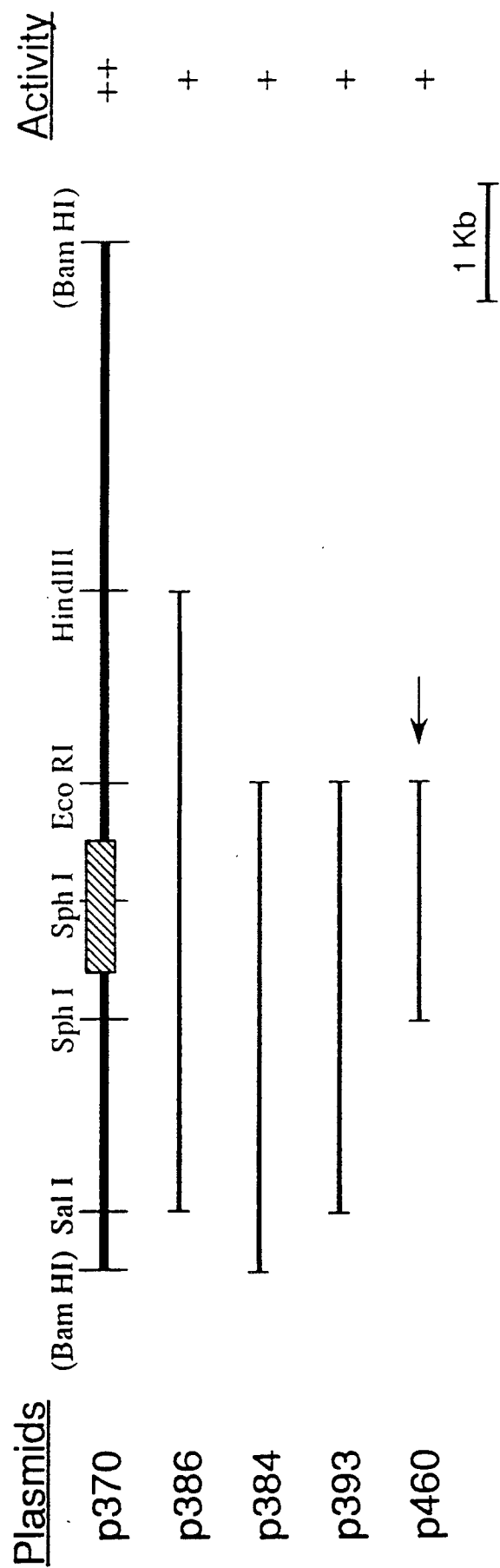

Fig. 4.

```
  1 GCATCAAAA CCGCAAGCTG TTTGTCTGGC CGCTGTTGCT GATCGGGGCG CTGGGCGTTCC TCGGGCGTCC TCGGCTCATG GCTGGTGGGT TCGAATAATT TCTGGCTCTC

101 CTACAGCCTG CTGGTGATCG CCCGCGCCGC GATGTACGCG CCTTACGGGCC CCTTCTTCGC CATTATTCCT GAAATGCTGC CCCGCAACGT CGCCGGGGGC

201 GCGGATGCCGC TGATCAACAG CATGGGCGCG CTCGGCTCTT TTGTCGGCTC CTGGATTGTG GGCTACCTTA ACGGAGCCAC CGGCAGCCCC GCCGCTTCCT

301 ATATCTTTAT GGGGCTGGCG CTCTCTGGTC CCGTCTGGCT TACTCTGATT GTCAAACCGG CGGAGAACAA ACAGCCCCCC TCGCCGGAAC GCCGCGGCCAG

401 GCACCCATGA CTAGTCGCGC GTAAGGTCCG GCGCATCCGA CTCTGCCCTCA AATTGCCCGAT CGGCGTCCGTT GACGATCGGC AATTATCTTT TCTGTTTACC

501 GCTCAAGCGG ATGGAGCCTG AC    ATG AAG CCT GAA GTG CTG TTA TAC AAA TCC CTT CCC GAC GAT TTA CGC GCC CGC CTC GAT
                              Met Lys Pro Glu Val Leu Leu Tyr Lys Ser Leu Pro Asp Asp Leu Arg Ala Arg Leu Asp
                               1                          10                                              20

583 GAG CAT TTC ACC GTC ACG GCG ATT AAC GGC CTC TCG CCG GAA ACC ATT GCG GAA CAT GGA GCT GGC GCC GGA GCT GCC AGA AGG
    Glu His Phe Thr Val Thr Ala Ile Asn Gly Leu Ser Pro Glu Thr Ile Ala Glu His Gly Ala Gly Ala Arg Arg Arg
                                   30                                           40

664 CAT GAT CGG CTC CAG CAG CAC GGT GGA TCA AGC GCT GCT GGA GAA AAT GCC AAA CTG CGC GCC GCC TCG ACG ATC TCC GTC
    His Asp Arg Leu Gln Gln His Gly Gly Ser Ser Ala Ala Gly Glu Asn Ala Lys Leu Arg Ala Ala Ser Thr Ile Ser Val
     50                                                60                                              70

745 GGC TAT GAC AAT TTT GAT GTG GAA GCG CTG AAC CAG CGC GGC ATT GTG CTG ATC GAT ACG ACC ACC GAA ACC
    Gly Tyr Asp Asn Phe Asp Val Glu Ala Leu Asn Gln Arg Gly Ile Val Leu Ile Asp Thr Pro Thr Val Leu Thr Glu Thr
                         80                                           90                                              100
```

Fig.4(cont. A)

```
826  GTC GCC GAT ACG ATG ATG GCG CTG GTG CTT TCC AGC GCG CGG CGC GTG GAA GTG GCG GAG CGG GTA AAG GCG GGC GAA
     Val Ala Asp Thr Met Met Ala Leu Val Leu Ser Ser Ala Arg Arg Val Glu Val Ala Glu Arg Val Lys Ala Gly Glu
                                        110                                    120

907  TGG CGG CGC AGC GGT CCC GAC TGG TTC GGC ATC GAT GTG CAT CAC AAA AAA ATG GGC ATT CTC GGC ATG GGC CGC ATC
     Trp Arg Arg Ser Gly Pro Asp Trp Phe Gly Ile Asp Val His His Lys Lys Met Gly Ile Leu Gly Met Gly Arg Ile
                         130                                   140                                   150

988  GGT CTG GCG CTG GCA CAG CGA CAG GCG CAT CAC GGC TTC GGC ATG CCG ATT TTA TAC AAT GCG CGC AAG CAT CAT GAG GAA GCG
     Gly Leu Ala Leu Ala Gln Arg Ala His His Gly Phe Gly Met Pro Ile Leu Tyr Asn Ala Arg Lys His His Glu Glu Ala
                         160                                   170                                   180

1069 GAG TCG CGT TTT AAC GCG CAG TAT TGC GAT CTC GAT ACC CTG CTC CGC GAG CTG CTC TGC TTT CTC TGC ATC AGC CCG CTG
     Glu Ser Arg Phe Asn Ala Gln Tyr Cys Asp Leu Asp Thr Leu Leu Arg Glu Leu Leu Cys Phe Leu Cys Ile Ser Pro Leu
                         190                                   200

1150 ACG GAA CAG ACT CAC CAT ATG ATC GGT CGT GAG CAG CTG GCG CAG CTG GCG AAA ATG AAG CCG AGC GCC ATT CTG ATT AAC GCG GGC CGC
     Thr Glu Gln Thr His His Met Ile Gly Arg Glu Gln Leu Ala Gln Leu Ala Lys Met Lys Pro Ser Ala Ile Leu Ile Asn Ala Gly Arg
                         210                                   220                                   230

1231 GGG CCG GTC GTG GAT GAG CAG CCG ATC GCC GCC CTG AAA GAT AAA ACC ATT CAC GCC GCA GGC CTG GAT GTG TTT GAA
     Gly Pro Val Val Asp Glu Gln Pro Ile Ala Ala Leu Lys Asp Lys Thr Ile His Ala Ala Gly Leu Asp Val Phe Glu
                         240                                   250                                   260

1312 CAG GAG CCG CTG CCG GTT GAT TCC GAA CTG TTG ACG CTG CCG AAC GTG GTG GCG TTG CCG CAT ATT GGT TCC GCG ACC CAT
     Gln Glu Pro Leu Pro Val Asp Ser Glu Leu Leu Thr Leu Pro Asn Val Val Ala Leu Pro His Ile Gly Ser Ala Thr His
                         270                                   280                                   290
```

Fig. 4 (cont. B)

```
1393 GAA ACG CGT TAC GGC ATG GCG CGC GAC GCC GTA GAT AAT CTG ATC GCG GCG CTG GCG GGC AAG GTA GAG AAG AAC TGC GTC
     Glu Thr Arg Tyr Gly Met Ala Arg Asp Ala Val Asp Asn Leu Ile Ala Ala Leu Ala Gly Lys Val Glu Lys Asn Cys Val
                                                                              310

1474 AAT CCG CAG GTG CTG CGT TAA  ATCGCT ATGGGCGGAT CATGGCCAACG CGGCGCGTGG TTTGCGGGCCG CGATGTTAAT GCGACCGCAA CCGTTCG
     Asn Pro Gln Val Leu Arg OC*
                 320

1568 GCA GAGCGCGTGG TTTGCGGGCCG CGATGTTAAT GCGACCGCAA CCGCTCAGCA GAGCGCGTGG TTTGCGGGCTG CGATGTCAAT GCGACCGCAA CCGCTC

1667 AGCA GAGCGCGTGG TTTGCGGGCTG CGATGTCAAT GCGACCGCAA CCGCTCAGCA GAGCGCGTGG TTTGCGGGCTG CGATGTCAAT GCGACCGCAA CCGCT

1766 CAGCA GAGCGCGTGG TTTGCGGGCCG CCATATTGCCG TCGGCCGCAA CCGGTCGCCT TACTCCACCG CGATCGGTTT TTCATCCAGC TGTGGCCGCT TGTC

1865 GCCCTG TAGCGTTTTA ACCCGTTGCT CTACTTTTTG TACTGCCTGC GCATCTTTTA ACAGCGTGTA GGTCAGCGTG AAAGCCTGGC TTTGCCCCGG TTG

1964 CAGCTGT TTTACCCTTC CCTGCTCTTT CTCGATGGTA ACCGGATAGG CGTAGTTAGT GCCCGGTTCA ATGCCGGTAA CGTAGCCCTG ATTCAGGGTG TC

2063 GGTATTCT TCCATAAGGT CAACACGCGGC AGCTGACGAG TGCGAATTC
``` tkrA Deletion Mutagenesis

Fig. 6.
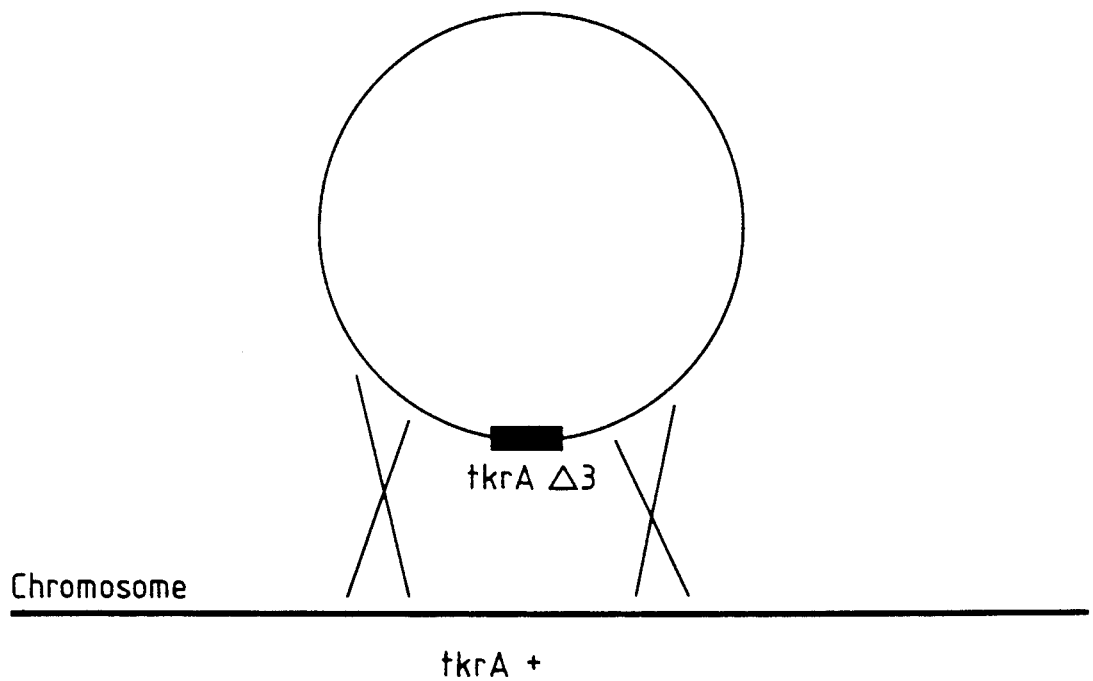
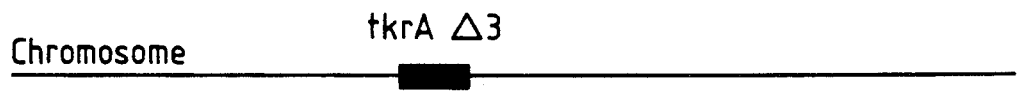

Model for Carbohydrate Metabolism in *Erwinia herbicola*

Fig. 11.

```
  1 GCATGCGTGCCGTTGATGATGATTCTGCCCCTGTTGCCCAGACCACGGGCCATAATGAAACCAATGCCCTGGGCGCCCGGTTATCAATATCCGTT
101 TGTTGTTAAGCTGAAAAGATCGTTCATCAACAAACCTGCCTTGTTTGCCATTCATAACGCCCTATATCACGGTTTTATGGCGTATAAAACTGTGACGGA
201 CGTCACTCTAATCCGTGTTACAAAACCCGGTTACCTTTGTTGTGAACTGTGGCAGGTCAGGCAGCCGAAATGGGCGGATCCGGTATCGGCGAATAATTCC
301 TTTTCCCTCTGCCGGCAGGCATAATAATGTGATGGAATCGCCGTCTGACGGAGGACATGAATAATGAAAATGCAACGCATAACGTTACATGATATCGCTACGC
401 TGGCGGGCGTAACAAAAATGACGGTTAGTCGGCTATTTACGCACGCCGGAAAAAGTAAAGGCCGGAACATCCCGAAACGGGCGATCGGGAGGT
501 TGGCTACCAGCCTGACGCCGATAATTCCGCCATGATCGGCAATACCCTGCCCCGATCGGCGTGCTTATTCCTTCCTTTCATAATCAGATTTTTGCCGAT
601 TTGCTCGGCAGGTGTGGAATCCGTTACCCGCGTACAGGGTTATCAGACGCCTGGTGTAAATTACGATTACGATCGCCAGCCGCGAAGAAGAAAAGATCGCTA
701 CGGTATTGGCTTTTAATATTAAGGCATTGCTTCTGACTGAATCCGTGCATACGGTGCGCGCAGAAAAATATCTGAAAGCTGCAGGCATCCCGATTGCCGGA
801 AGTGATGGGCCTGACTCAGAGACGCCCGGACGCATCAGCGTAGGCTTCAATAATCACCGCGCCGGTCTGGATATGACGAATATGCTGCTGCCAGCGGTAAA
901 AAACACATTATCTATTTTGGTTCGATGTCCGATACGCCGTGATGAACAACGCTATGCAGGCTATTGCGAAGCCATGACGGGCGGGGACTCCCAGCGGGGC
```

Fig.11(cont. A)

```
1001 GCATAGCGCCGAATAAAATTCTTCGGTTCCATCGGTACAGGCATGATGACTCTGGCGGGCAGATCTATCCCAATATGGATGGCATTCTCTGTACCAA
1101 TGATGATCTGGCCGTTGCCGTATTGCAGGAGTGTCGCGCCGAGGCATTCTTGTCCCGATCAAATGGCCATCGCAGGTTTCACGGGCTGGAAATCGGG
1201 CAGGTAACAACGCCGCAATTGGCCAGCCGTGGTCACGCGCCTTCGAAATGGGCCAAGGTCGGCCACAGAAATTCTTCATTAAAAGATCCATCAACAACCCA
1301 CCATCGAGGCAGGTCGATTTGCATTATCGTCTGTCGATGGGCGCTACCATCTGAAATGTGTCACCCGATATAGCCGAATCGCCGTCACGATCACGCCATCA
1401 GTAACAGAGTTCTTAACACTTTTTCATGTGATATTTATCACAAAAAAATACGTCAGAACGCCTTTAATAGTATCCATCTCAGGTAAGCGGAATGATTAAA
                     MetThrGlnAlaArgProAsnIleLeuLeuIleAlaIlePheGlyValGlyThrAspAlaValAspLeuAspSerLeuLeuAspSerSerAlaPheGluValHisArg
1501 GGAACGGCTCATGACGCAACAAGCCGGCAATATTTACTGCCCGGTGCTCTGATTCGCCCGGTCTCAGCTCCGCCTTTGAGGTGCATC
  32   LeuTyrGluGlnAspGluProLeuAlaTrpLeuAlaAlaGluGlyThrArgValGlnAlaValValThrArgGlyAspValGlyIleSerAsnAlaVal
1601 GTCTGTATGAACAGGATGAACCCGTTGGCCTGGCTGCCGCCGAGGGACCGCGCGTTCAGGCCGTCGTGATCGCGGTATCAGCAATGCCGT
  65   LeuGluGlnLeuProGlnIleGlyLeuIleAlaIlePheGlyValGlyThrAspAlaValAspLeuAspTyrAlaArgLysAlaAsnIleAlaValThr
1701 ACTCGGAACAATTACCGCAGATCGGGCTGATTGCCATCTTCGGCGTAGGCACTGACGCCGTTGACCTTGATTATGCTCGCAAAGCGAATATTGCCGTCACC
  98   IleThrSerGlyValLeuThrAsnAspValAlaAspMetAlaMetGlyLeuLeuLeuSerGlyAlaArgArgLeuCysLeuGlyAspArgPheValArgGlu
1801 ATCACTTCCGGCGTGCTGCTGACTAACGATGTTGCTGACATGGCGATGGGACTGCTGCTGAGCGGCGCACGGCGCCTGTGTCTCGGGGATCGCTTCGTACGTG
```

Fig.11(cont. B)

```
132    GlyGlnTrpLeuArgGlnAlaProAlaLeuGlyThrGlnValSerGlyLysArgValGlyIleValGlyMetGlyArgAlaIleAlaGln
1901   AAGGCCAGTGGCTCAGGCAAGCTCCCCGGCCCTCGGCACCCAGGTCAGCGGGAAGCGAGTCGGCATCGTGGGCATGGGCAGAGCCATCGCTCA

165    ArgAlaThrAlaPheAspMetSerValSerTyrIleSerCysThrLysProLeuProTyrThrArgCysGlyAspIleTyrThrLeuAlaArg
2001   ACGGCGACGGCGTTGATATGTCGGTATCCTATATCAGTTGTACGCCAAACCGGAGCTTCCCTATACCCGGTGCGGGACATTTACACCCTGGCGCGG

198    GluAsnAspPheLeuIleValAlaAlaSerGlyGlyAlaAlaAsnArgGlyLeuIleAspAlaSerValLeuGluAlaMetProAlaHisAlaTrpLeuVal
2101   GAAAATGATTTCCTGATCGTCGCCGCCTCCGGGGGCGGGGCCAAACCGTGACTGATCGATGCCTCGGTTCTTGAGGCCATGCCGGCCACGCTGGTTGG

232    AsnIleAlaArgGlyThrLeuValAspGluAsnAlaLeuIleGlnAlaLeuGlnArgLysAlaIleAlaGlyAlaAlaLeuValPheGluGluGlu
2201   TCAATATCGCTCGCGGAACGCTGGTAGATGAAAACGCCCTGATTCAGGCGCTAAAAGCCATTGCTGGCGCCGTTGCTTAGACGCTCTTCGAAGAAGA
```

Text continues (partial):

```
265    ProHisValProGluAlaLeuIleAlaLeuAspAsnValIleLeuGlnProHisValGlySerAlaThrAlaGluThrArgGlnLysMetSerAspVal
2301   ACCTCATGTCCCTGAAGCGCTTATCGCGCTGGATAATGTGATATTGCAACCACACGTCGGCAGCGCGACAGCGGAAACACGTCAAAAATGAGCGATGTC

298    ValPheAlaAsnValAlaAspAlaPhePheLysGlyArgProLeuProAsnAlaValOC*
2401   GTTTTTGCTAATGTCGACGCGTTTTTTAAAGGGGCCCCCTTACCCAACGCGTGTTTAATCCCGCCATTCATTTTTATTCAGGCACTCACGATGTGTTACCA

2501   ACATCGTTAGCGCCGTACGTTCCGTAAATTCACAGAGGGCGCTGTATGGATAATAAAATACCGGGACTCGGTGGTTACGTGTCATTGCCCCATTCTGA

2601   TTACCTGTATTGTTCTTTTATGCATCC
```

Fig. 13.
ptacTKRB-Kan
1. Transformation or conjugation of Erw. herbicola or A. cerinus
2. Selection for Kan$^R$ phenotype
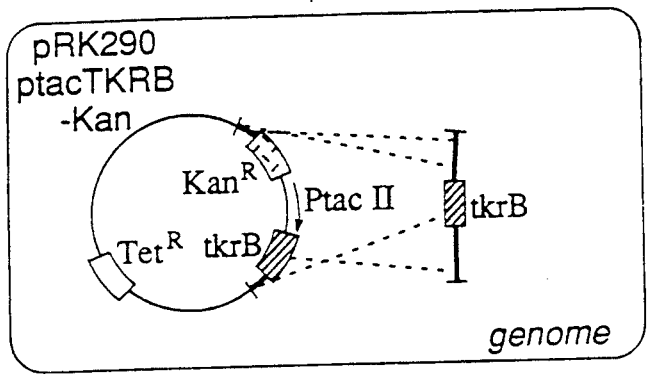
Recombination between homologous sequences on plasmid and host chromosome
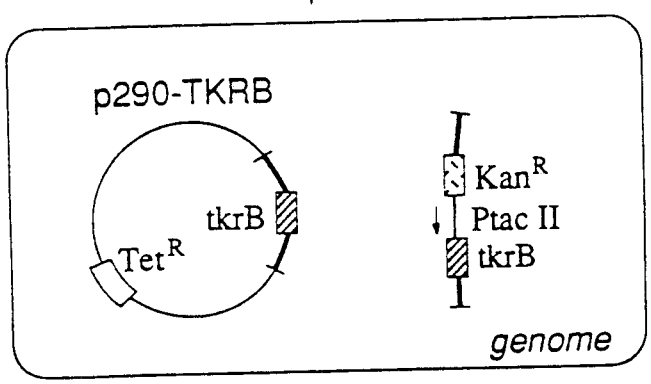
1. Transformation or conjugation with pR751
2. Select for Kanamycin and trimethoprim resistance
3. Screen for tetracycline sensitive clones
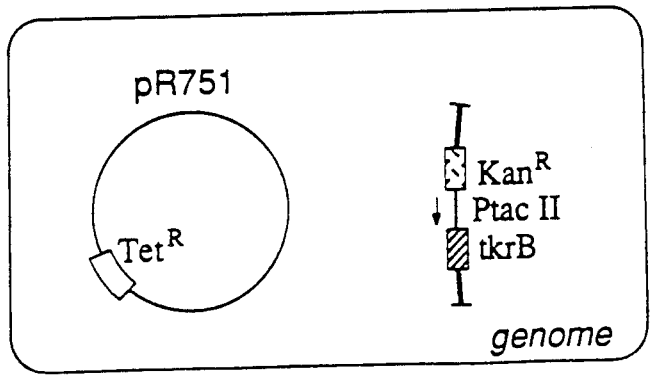

METABOLIC PATHWAY ENGINEERING TO INCREASE PRODUCTION OF ASCORBIC ACID INTERMEDIATES

CROSS REFERENCE TO RELATED APPLICATIONS

Cross reference is made to application Ser. No. 06/620,585, filed June 14, 1984, which was a continuation-in-part of Ser. No. 06/508,410, filed June 28, 1983, Ser. No. 06/620,651, filed June 14, 1984, now issued U.S. Pat. No. 4,757,012 which is a continuation-in-part of application Ser. No. 06/508,628, filed June 28, 1983, and to Ser. No 06/620,652, filed June 14, 1984, now issued U.S. Pat. No. 4,758,514, which is a continuation-in-part of application Ser. No. 06/508,409, filed June 28, 1983.

BACKGROUND

This invention concerns aspects of a process for the production of ascorbic acid. The invention relates to improvements in the method for converting an ordinary metabolite, such as D-glucose, into 2-keto-L-gulonate (2-KLG), a stable precursor of ascorbic acid. The invention relates to the use of recombinant technology to alter the metabolism of a microorganism to carry out a desired bioconversion. It specifically relates to the use of recombinant technology to transfer genetic material to a microorganism such that transfer renders the cell capable of effecting the conversion of an ordinary metabolite to 2-KLG and to control the effect of secondary metabolites or metabolic pathways on that conversion. More specifically, the invention relates to the elimination and/or modulation of the level of secondary metabolites such as L-idonate or altering the enzymatic activity in a metabolic pathway, such as, for example, altering the activity of 2-ketoaldonate reductase.

Ascorbic acid has become a major chemical product in the United States, and elsewhere in the world, due to its importance in health maintenance. While there may be some controversy over its efficacy in ameliorating the tendency of individuals to contract certain minor illnesses, such as, for example, the common cold, there is no doubt that it is essential for human beings to ingest required amounts of vitamin C. It has become a matter of concern in recent years that "natural" foods may not provide adequate amounts of vitamin C. Accordingly, there has developed a large demand for ascorbic acid, both as an additive to foods which are marketed to the consumer with supplemented levels of this vitamin, and as a direct vitamin supplement. Furthermore, ascorbic acid is an effective antioxidant and thus finds applications as a preservative both in nutritional and in other products.

There are a number of processes available, some commercially viable, for the production of vitamin C. Several of these result in the preliminary production of 2-keto-L-gulonic acid (2-KLG) which can then be rather simply converted to ascorbic acid through acid or base catalyzed cyclization. Accordingly, 2-KLG has become, in itself, a material of considerable economic and industrial importance.

Means are presently available in the art to convert ordinary metabolites, such as, for example, D-glucose, into 2,5-diketo-D-gluconic acid (2,5-DKG) by processes involving the metabolism of prokaryotic microorganisms. See, for example, U.S. Pat. No. 3,790,444 (Feb. 5, 1974); 3,998,697 (Dec. 21, 1976); and EPO Application Publication No. 0046284 published Feb. 24, 1982. The availability of this 2,5-DKG intermediate offers a starting material which is converted to the desired 2-KLG by a single step reduction. The reduction can be effected chemically or catalyzed enzymatically. Various bacterial strains are known which are capable of effecting this reduction. Such strains are found in the genera Brevibacterium, Arthrobacter, Micrococcus, Staphylococcus, Pseudomonas, Bacillus, Citrobacter and Corynebacterium. See, for example, U.S. Pat. No. 3,922,194 (Nov. 25, 1975), U.S. Pat. No. 4,245,049 (Jan. 13, 1981) and U.S. Pat. No. 3,959,076 (May 25, 1976).

It is helpful to understand the context into which the present invention finds utility by representing the process in terms of the relevant chemical conversions. An outline of a typical overall process for manufacture of ascorbic acid is shown in Reaction Scheme 1.

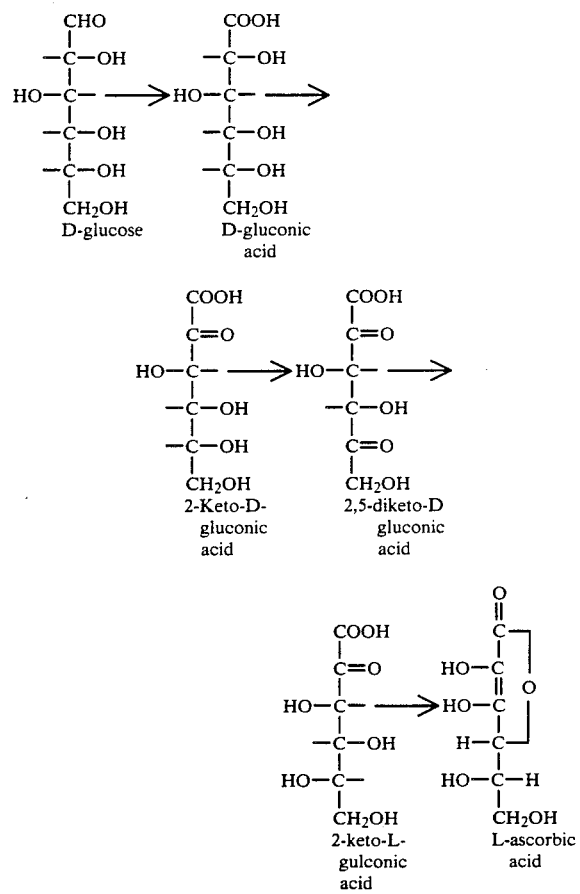

Reaction Scheme 1

The process conveniently begins with a metabolite ordinarily used by a microorganism such as, for example D-glucose as shown in Reaction Scheme 1. Through enzymatic conversions, which may include the enzymes D-glucose dehydrogenase D-gluconate dehydrogenase and 2-keto-D-gluconate dehydrogenase, the D-glucose undergoes a series of oxidative steps to give 2,5-diketo-D-gluconic acid. It has been shown that this series of steps can be carried out in a single organism. (U.S. Pat. No. 3,790,444, EPO Appln. A20046284 [supra]); such organisms are, for example, of the genus Gluconobacter Acetobacter or Erwinia.

Alternate preparations of ascorbic acid have circumvented the 2,5-DKG intermediate by a combination of fermentative and chemical oxidations, and are clearly more cumbersome than the process shown. Typical of these is the Reichstein synthesis which utilizes diacetone-2-keto-L-gulonic acid as a precursor to 2-KLG. This intermediate is generated through a series of reductive and oxidative steps involving fermentation, hydrogenation, and, e.g., permanganate oxidation. Such a sequence is more complex than the reaction scheme shown above. The conversion of 2,5-DKG into 2-KLG can also be carried out enzymatically (U.S. Pat. Nos. 3,922,194; 3,959,076 [supra]; and 4,245,049 [Jan. 13, 1981]).

Means are presently well known in the art to convert the resulting 2-KLG into ascorbic acid. This may be done either in the presence of dilute acid and heat or in a two-step process utilizing preliminary esterification in methanol, followed by lactonization in base. Effective procedures are described in Crawford, T. C., et al., *Advances in Carbohydrate Chemistry and Biochemistry*, 37, 79-155 (1980). These alternatives are straightforward and take advantage of the greater stability and shelf life of 2-KLG over ascorbic acid. Thus, it is more desirable and convenient to stockpile the 2-KLG intermediate for subsequent conversion to the desired final product than to synthesize the ascorbic acid directly.

Because of the improvements of the present invention, alternate, superior means are available to effect this overall conversion. Recombinant techniques permit the coding sequences and necessary expression control mechanisms to be transferred into suitable host organisms resulting improved characteristics Determination of the metabolites and metabolic pathways associated with 2-KLG in a recipient cell is then carried out. Alteration of the highly coordinated, purposeful activity of various related metabolic pathways arising consequent to the genetic transfer is then carried out. Thus, simply focusing on the bioconversion of glucose to 2-KLG, several levels of improvement are attainable: 1) stricter control over metabolic variables using the transfer or deletion of genetic material; 2) selection of host organism into which genes may be transferred and in which metabolites and metabolic pathways can be modified to optimize the bioconversion.

The scope of improvement permitted by the transfer of a gene encoding 2,5-DKG reductase to a bacterial cell is optimized by the determination and modulation of metabolites and metabolic pathways associated with the bioconversion arising from the activity of enzyme(s) encoded by the transferred gene(s). Because of the availability of the appropriate genetic machinery, it is possible, as well as desirable, to transform an organism capable of producing the 2,5-DKG with the gene encoding the reductase and then eliminating gene(s) encoding enzymes in undesired metabolic pathways. Undesired metabolic pathways present in the untransformed organism into which the genetic material is transferred may be modulated using recombinant technology. In this way optimal bioconversion of glucose to 2-KLG can be carried out in a single organism. Thus, the same organism can effect the entire process of converting, for example, glucose or other suitable ordinary metabolite producing large yields of the stable, storable intermediate 2-KLG.

SUMMARY OF THE INVENTION

The present invention effects dramatic improvements in the process for converting a commonly available metabolite such as glucose into 2-KLG a stable storable precursor for ascorbic acid. The pathway of the process described by the present invention encompasses the step of converting 2,5-DKG into 2-KLG.

This invention is based in part on the novel and unexpected identification of metabolites and metabolic pathways involved in the carbohydrate metabolism of an ordinary metabolite, such as glucose to 2-KLG in a recombinant organism. In particular, L-idonate was discovered as a metabolite in the metabolic scheme in which an ordinary metabolite such as glucose is converted to 2-KLG in a recombinant organism. The invention is further based on the observation that the carbohydrate flux from glucose to 2-KLG can be controlled by the elimination and/or modulation of the newly identified metabolites and metabolic pathways by using genetic means.

This invention is also based in part on the observation that optimization of the bioconversion of an ordinary microbial metabolite into 2-KLG can be achieved by modulation of the expression level of an enzyme or enzymes responsible for the bioconversion. In particular, transformation with a vector providing for high expression levels of 2.5 DKG-reductase will increase metabolic flux through a metabolic pathway to a desired product while reducing flux through secondary metabolic pathways. It was also observed that uncontrolled high level expression of an enzyme or enzymes responsible for the bioconversion of an ordinary metabolite into 2-KLG, while producing more enzyme, results in decreased cell viability which in turn affects the efficient bioconversion of an ordinary metabolite to 2-KLG. Optimal expression levels of the enzyme using a controllable expression system to insure cell viability produced maximal levels of the desired product.

The invention relates to a process for the efficient bioconversion of an ordinary microbial metabolite such as glucose into 2-KLG by fermentation by a single recombinant organism. It also relates to the conversion of 2-KLG to ascorbic acid It also relates to the recombinant organism. It further relates to the recombinant organism capable of carrying out the bioconversion of glucose or other ordinary metabolite to 2-KLG. Such an organism is conveniently constructed by transferring to a host cell capable of effecting the conversion of the initial metabolite to 2,5-DKG an expression vector encoding and capable of expressing the 2,5-DKG reductase gene. Alternatively, such a recombinant organism is constructed by transforming an organism already producing the 2,5-DKG reductase with vectors encoding the enzymes responsible for the oxidation of the initial metabolite to 2,5-DKG. In either event, use of proper promoters and ribosome binding sites in the construction of the expression vectors permits the expression of the gene or genes for the enzyme(s) in the host cell. Metabolites and metabolic pathways present in both the host organism as well as arising consequent to the transfer of genetic material are determined. The level(s) of the metabolites and/or enzymes involved in those metabolic pathways are eliminated using mutagenesis. Thus, the invention also relates to the optimization of the bioconversion of an ordinary metabolite such as glucose to 2-KLG. In another aspect the invention relates to the recombinant organism into which genetic

BRIEF DESCRIPTION OF THE DRAWINGS

FIG. 2 shows the purification and identification of cytosolic carbohydrate ketoreductases in *E. herbicola* into which an expression vector for 2,5-DKG reductase has been transferred.

FIG. 3 shows the restriction map in the region of the cloned 2-ketoaldonate reductase gene.

FIG. 4 shows the DNA sequence of the *E. herbicola* tkrA gene and the protein sequence for 2KR(A).

FIG. 6 shows the introduction of the mutated *E. herbicola* tkrA gene in *E. herbicola*.

FIG. 11 shows the DNA sequence of the *E. herbicola* tkrB gene and the protein sequence for 2KR(B).

FIG. 13 shows integration of the tkrB gene under control of the tacII promoter into the *E. herbicola* chromosome.

DETAILED DESCRIPTION

A. Definitions

Figure 1:
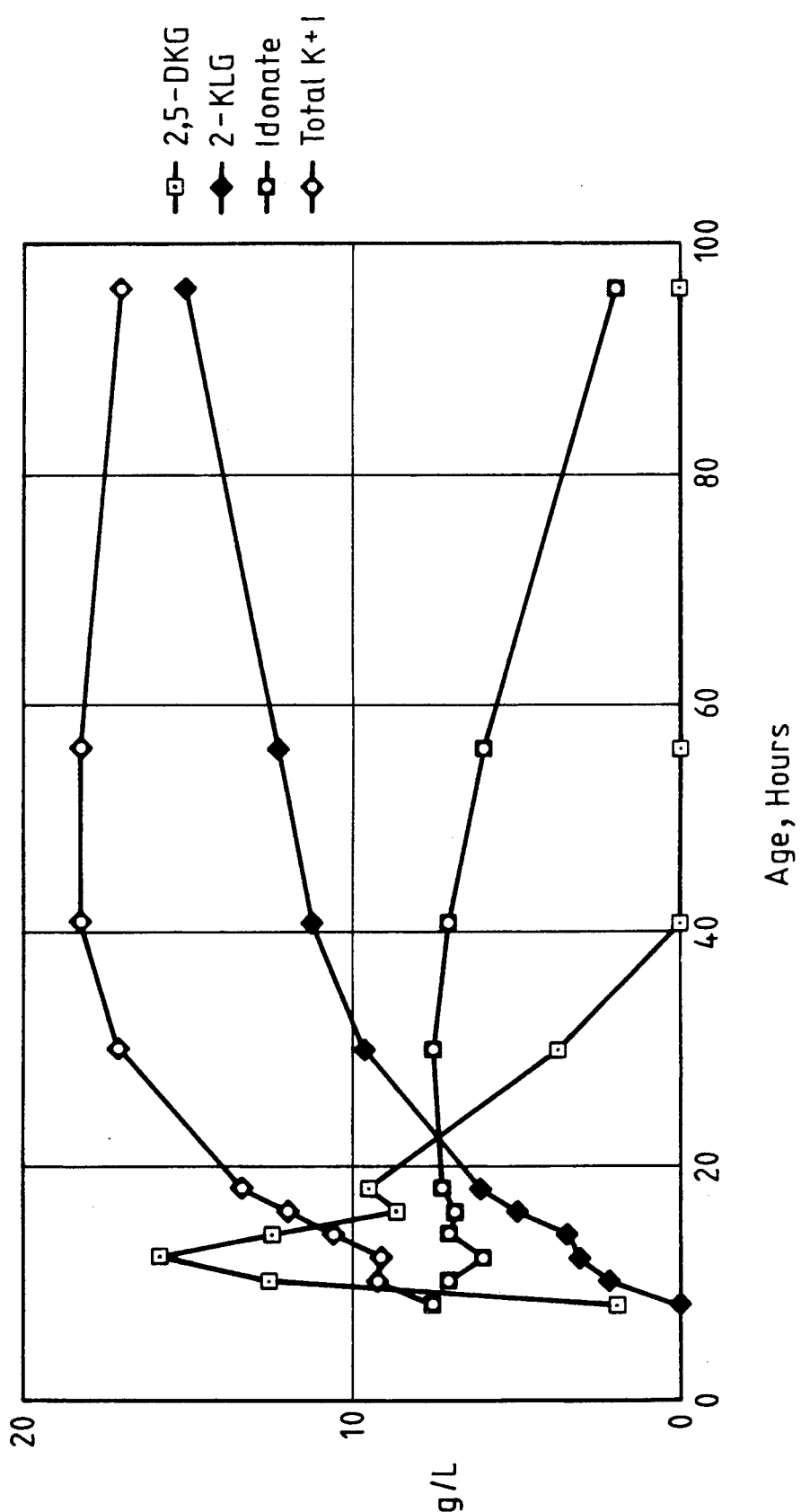
FIG. 1 shows glucose bioconversion in *E. herbicola* into which an expression vector for the 2,5-DKG reductase gene has been transferred.

As used herein, "2,5-DKG reductase" refers to a protein which is capable of catalyzing the conversion of 2,5-DKG stereoselectively to 2-KLG. Many species have been found to contain the reductase, particularly members of the coryneform group, including the genera Corynebacterium, Brevibacterium, and Arthrobacter; hence it appears by virtue of present knowledge that a preferred source for the enzyme is a member of the coryneform group. In the specific example herein, the particular form of this enzyme present in Corynebacterium was cloned and expressed. However, other bacterial species, such as, for example, those from the genera Brevibacterium, Arthrobacter, Micrococcus, Staphylococcus, Pseudomonas, Citrobacter and Bacillus are also known to synthesize an enzyme with the same activity as this enzyme. These genera are illustrative of potential sources for an enzyme similar to that present in Corynebacterium which may be available to catalyze this conversion. Alternate sources in addition to these naturally occurring ones in the prokaryotic kingdom may well be found. In addition, as the invention herein discloses and makes available the genetic sequence encoding such enzymes, modifications of the sequence which do not interfere with, and may, in fact, improve the performance of this enzyme are also available to those knowledgeable in the art. Such modifications and altered sequences are included in the definition of 2,5-DKG reductase as used in this specification. In short, the term 2,5-DKG reductase has a functional definition and refers to any enzyme which catalyzes the conversion of 2,5-DKG to 2-KLG.

As used herein, "secondary metabolites" or "secondary metabolic pathways" refer to those metabolites or metabolic pathways which divert accumulation of the desired product. These metabolites or metabolic pathways may be present in the host cell or may arise consequent to transfer of genetic material to the host cell wherein the transfer of genetic material renders the cell capable of converting an ordinary metabolite to a desired product. Thus in converting an ordinary metabolite, such as glucose, to 2-keto-L-gulonic acid (2-KLG) secondary metabolites or metabolic pathways would be those metabolites or metabolic pathways which reduce the amount of 2-KLG produced. Such a metabolite is L-idonic acid (IA). Such a metabolic pathway comprises the enzymatic reduction of 2-KLG to IA by 2-ketoaldonate reductase (2-KR). The secondary metabolite or metabolic pathway may arise proximate to or several steps removed from the desired metabolic conversion. The secondary metabolite or metabolic pathway may be present in the cell into which the genetic material is transferred. Alternatively, the secondary metabolite or metabolic pathway may arise as a direct consequence of the transfer of genetic material. The secondary metabolite or metabolic pathway may arise at the final step of the desired metabolic conversion. For example. 2-KLG, the desired product, may be catalytically reduced to IA. The secondary metabolite or metabolic pathway may also arise at an intermediate step in the desired metabolic pathway. Thus, D-gluconic acid, 2-keto-D-gluconic acid or 2,5-diketo-D-gluconic acid could be converted to a secondary metabolite via a secondary metabolic pathway. Such a secondary metabolic pathway comprises the enzymatic reduction of 2,5-DKG to 5-keto-D-gluconate by 2-ketoaldonate reductase or 2-KDG to gluconate by 2-ketoaldonate reductase.

It is well understood in the art that many of the compounds discussed in the instant specification, such as proteins and the acidic derivatives of saccharides, may exist in variety of ionization states depending upon their surrounding media, if in solution, or out of the solutions from which they are prepared if in solid form. The use of a term such as, for example, gluconic acid, to designate such molecules is intended to include all ionization states of the organic molecule referred to. Thus, for example, both "D-gluconic acid" and D-gluconate" refer to the same organic moiety, and are not intended to specify particular ionization states. It is well known that D-gluconic acid can exist in unionized form, or may be available as, for example, the sodium, potassium, or other salt. The ionized or unionized form in which the compound is pertinent to the disclosure will either be apparent from the context to one skilled in the art or will be irrelevant. Thus, the 2,5-DKG reductase protein itself may exist in a variety of ionization states depending on pH. All of these ionization states are encompassed by the term "2,5-DKG reductase."

Similarly, "cells", "host cells" and "cell cultures" are used interchangeably unless the context indicates otherwise. Gene transfer refers to a transfer or exchange of genetic material from one source to a recipient. There are three frequently used methods of gene transfer in bacteria: transformation (sometimes referred to as transfection), transduction and conjugation. Other gene transfer techniques are protoplast fusion and R' plasmids (Holloway, B. W., J. Bacteriol. 133:1078 [1978]). The transfer of a gene to a cell or to cells comprising a cell culture amounts to the same activity; it is a gene transfer process in which exogenously added DNA is taken up by a bacterium. A cell or microorganism receiving the transferred gene by one of the three types of gene transfer that now replicates and expresses the DNA so taken up is referred to as a recipient cell or microorganism. It is each bacterium that takes up the transferred material, frequently an expression vector, although it is a culture of bacteria that is treated with the genetic material.

"Transduction" refers to a gene transfer process in which a bacterial virus propagating on one strain of bacterium, the donor, picks up genetic information and upon infection of another strain of bacterium, the recipient, sometimes causes a heritable change. A recipient cell that acquires a donor trait by this process is called a transductant. "Conjugation" refers to a gene transfer process in which one strain of bacterium, the donor, possessing a conjugative plasmid, makes physical contact with another strain of bacterium, the recipient, and transfers genetic material. Conjugative plasmids possess "tra" genes that typically specify and/or control: synthesis of appendages referred to as donor pili, which allow donor cells to make contact with recipient cells; synthesis and release of substances that minimize donor-donor matings; and, conjugational transfer of DNA commencing from a definable transfer origin site on the conjugative plasmid molecule. The recipient which acquires donor genetic information is called a transconjugant. Strains with readily selectable genetic markers such as nalidixic acid or rifampicin resistance, or special nutritional requirements, are used in order to isolate transconjugants. "Transformation" refers to a gene transfer process carried out by various methods such as by nuclear injection or calcium treatment using calcium chloride as described by Cohen, F. N. et al., *Proc. Natl. Acad. Sci. USA*, 69:2110 (1972).

"Expression vector" includes vectors which are capable of expressing DNA sequences contained therein where such sequences are operably linked to other sequences capable of effecting their expression. It is implied, although not explicitly stated, that expression vectors must be replicable in the host organisms either as episomes or as an integral part of a chromosomal DNA; clearly a lack of replication would render them effectively inoperable. In sum, "expression vector" is also given a functional definition. Generally, expression vectors of utility in recombinant techniques are often in the form of "plasmids" which term refers to circular double stranded DNA molecules which, in their vector form, are not linked to the chromosomes. Other effective vectors commonly used are phage and non-circular DNA. In the present specification, "plasmid" and "vector" are often used interchangeably; however, the invention is intended to include such other forms of expression vectors which serve equivalent functions and which are, or subsequently become, known.

"Recombinant cells" refers to cells into which vectors, constructed using recombinant DNA techniques, have been introduced using one of the methods described above. "Host" cells refers to such cells before the DNA has been transferred. In general, recombinant cells produce protein products encoded by such recombinant vectors which protein products would not ordinarily be produced; however, the definition also includes cells containing vectors encoding proteins which are, coincidentally, encoded in the bacterial chromosome or otherwise endogenously expressed in the recipient cell. The definition includes any cell which is producing the product of a xenogeneic sequence by virtue of recombinant techniques.

"Ordinary metabolite" refers to such carbon sources as are commonly utilized by bacteria for growth. Examples of such metabolites are glucose, galactose, lactose fructose or other carbohydrates which are readily available foodstuffs for such organisms. Such metabolites are defined herein to include enzymatic derivatives of such foodstuffs which are convertible into 2-keto-L-gluconic acid (2-KLG). Such derivatives include D-gluconic acid, D-mannonic acid, L-gulonic acid, L-idonic acid 2-keto-D-gluconic acid, 5-keto-D-gluconic acid, 5-keto-D-mannonic acid and 2,5 diketo-D-gluconic acid.

"Genetic manipulation" refers to various means to effect a change in a secondary metabolite or metabolic pathway. Such a change may be to eliminate a secondary metabolite or metabolic pathway. Such elimination may be achieved using various genetic means to eliminate a specific secondary metabolite, enzyme in a secondary metabolic pathway or a cofactor necessary for a secondary metabolic pathway. The various genetic means include certain random mutagenic techniques such as chemical mutagenesis using various chemical agents such as N-methyl-N-nitro-N-nitrosoguanidine (NG) or ethylmethanesulfonate (EMS); γ-rays, X-rays and ultraviolet light. More specific methods of mutation will produce chemical changes in DNA leading to specific mutant gene products. In transitional mutants, one purine-pyrimidine base pair is replaced by another, that is, A-T for G-C or G-C for A-T, so that a purine in one chain is replaced by another purine and a pyrimidine in the other chain by another pyrimidine. Transitional mutations occur spontaneously but may also be induced by base analogs, in particular 5-bromouracil (BU) and 2-aminopurine (AP). Since 5-bromouracil has a close structural resemblance to thymine, it is readily inserted into DNA during its replication (as 5-bromouridylic acid) in the positions normally occupied by thymine. However, the keto form of 5-bromouracil, which pairs readily with A, may undergo tautomerization to the enol form, which more readily pairs with G. In this way replacement of T by BU in one chain may lead to incorporation of G rather than A in the complementary chain. When the latter chain in turn is replicated, the G now specifies C in the new complementary chain. The analog 2-aminopurine acts similarly., it can be read either as A or G. Transitional mutations are also produced by nitrous acid; it deaminates adenine, whose normal partner is T, to form hypoxanthine, which pairs with C.

Insertion point mutations involve insertion of an extra base pair. The result is one type of frame-shift mutation, so called because the normal reading-frame relationship for readout of nucleotide triplets is put out of register by the mutation. Insertions are readily induced by treating cells with acridine derivatives. Acridine is a planar heterocyclic molecule. Much evidence suggests that, because of its flat, aromatic structure, acridine becomes noncovalently inserted, or intercalated between two successive bases in DNA, separating them physically. When this chain is replicated, an extra base is covalently inserted into the complementary chain opposite the intercalated acridine. When this chain is then replicated in turn, the new complementary chain will also contain an extra base.

Deletion mutation results from a deletion of one or more bases from the DNA; it too is a frame-shift mutation. A deletion may result from hydrolytic loss of a purine base because of high pH or temperature, by action of covalent cross-linking reagents, or by alkylating or deaminating agents, which cause formation of bases that cannot pair. The compound proflavin also induces deletions.

A variety of recombinant DNA techniques are available to achieve directed mutagenesis at specific sites in the bacterial genome (Roeder and Collmer, *J. Bacteriol.* 164:51 [1985]; Ruvkun and Ausubel., *Nature* 289:85 [1981]). Specific mutations are introduced into the gene of interest carried on a plasmid. The plasmid can then undergo integration at the site of homologous sequences in the host chromosome followed by the subsequent deletion of the host chromosomal copy of the gene. The specific mutation is thus permanently introduced into the strain. Techniques such as UV irradiation that promote this homologous recombination event facilitate the introduction of the mutation into the chromosome.

B.1 Strains and Culture Conditions

*Erwinia herbicola* (ATCC 21998) and *E. coli* MM294 (ATCC 31446) were obtained from the American Type Culture Collection. *Acetobacter cerinus* (ATCC 39140) can also be obtained from the American Type Culture Collection. Strains were routinely grown on LB plates or media at 30° C. or 37° C. for *E. herbicola* and *E. coli*, respectively. The concentration of antibiotics used for plasmid selection was 20 μg/ml tetracycline and 50 μg/ml ampicillin. Shake flask biotransformations of 2-KLG and 5-KDG were carried out as follows: Cells were grown to saturation in LB media at 30° C. overnight, centrifuged, the pellets were washed in sterile ML5 media, recentrifuged, and resuspended in ML5 media containing either 1% glycerol or 0.5% glucose and 50 mM 2-KLG or 50 mM 5-KDG. Shaking was continued for 50 h and samples were taken periodically for HPLC and GC analysis. ML5 media contains: 0.36 g/l $(NH_4)_2SO_4$, 6.0 g/l $KH_2PO_4$, 1.0 g/l $MgSO_4.7H_2O$, and 13.1 g/l MES (4-morpholinoethane-sulphonic acid) adjusted to pH 7.0 with NaOH and filter sterilized. The bioconversion of 2,5-DKG was carried out similarly using both 21998p269 and 21998tkrAΔ3p269, described below, containing 10 μg/ml tetracycline and 1 mM IPTG in the initial LB media. After washing, the cultures were resuspended at 4.6 $A_{550}$ in ML5/0.1% yeast extract/10 μg/ml tetracycline/1 mM IPTG/13 g/l 2,5-DKG (K+). The bioconversion of glucose in 10 liter fermenters was carried out as follows and as shown in FIG. 1. A single colony isolate of *E. herbicola* 21998 ptrp 1-35 was removed from a Luria Broth agar plate, 5 μg/ml tetracycline, and resuspended in 50 ml Luria Broth, 5 μg/ml tetracycline. The culture was incubated at 30° C. After the cell concentration reached approximately 1.0 $A_{550}$, a 1.0 ml aliquot was transferred to 500 ml Luria Broth, 5 μg/ml tetracycline, in a 2L baffled Erlenmyer flask. The flask was incubated for 12 hours 200 rpm, and 30° C. The inoculum was transferred to a 10L fermentor containing: $(NH_4)_2SO_4$, 2.5 g/l; $KH_2PO_4$, 3.0 g/l; $K_2HPO_4$, 2.0 g/l; $MgSO_4$ $7H_2O$, 1.0 g/l and Ucon antifoam 1 ml/l. The following components were sterilized separately and added to the vessel poststerilization: Tetracycline HCL, 5 μg/ml; glucose, 10 g/L; yeast extract, 12.5 g/L. The pH was maintained at 6.0 with $Na_2CO_3$ and $H_3PO_4$. The temperature was maintained at 28° C. and the dissolved oxygen was controlled at greater than 30% of saturation at atmospheric pressure. A single 30 g/L addition of glucose was made when the cell density achieved 15 $A_{550}$.

B.2 Analytical Methods

Carbohydrate analyses of the reaction products from the various incubations were performed using the HPLC and GCMS methodologies previously described (Lazarus, R. and Seymour, J., *Anal. Biochem.* 157:360 [1986]). Cell lysates were obtained by spinning the culture at ca. 15,000×g for 10 minutes, followed by freezing the pellet, resuspension in 20 mM Tris.-HC1, pH 7.5, sonication, and recentrifugation to isolate the supernatant. The membrane fraction was isolated by further ultracentrification in a Type 35 rotor at 80,000×g for 90 minutes. The pellet was solubilized in 50 mM bis-Tris.HC1, pH 6.5 containing 0.2% NP40. The dehydrogenase activities could also be solubilized in 0.5% Tween 20, Triton X-100, or N-octyl glucoside, however some enzyme inhibition is evident with these detergents. Cytosolic incubations contained either crude lysates or partially purified enzyme and 27 mM of substrate and coenzyme in 100 mM bis-Tris.HC1, pH 7.0. Routine assays were carried out in the same buffer at 25° C. containing 0.2 mg/ml NAD(P)H and 100 mM 2-KLG, 2-KDG, or 5-KDG or 10 mM 2,5-DKG and were followed at 340 nm for coenzyme oxidation. Enzyme assays on the membrane bound dehydrogenases were carried out at 25° C. in 100 mM bis-TrisHC1, pH 6.0 containing 0.2 mM phenazine methosulfate, 0.2 mM 2,6-dichloroindophenol ($E_{600}=14.1$ $mM^{-1}$), 0.09 mg of protein, and substrate. The assay was followed either spectrophotometrically at 600 nm on a Kontron model 860 spectrophotometer or by measuring $O_2$ consumption on a Yellow Springs Instrument model #53 $O_2$ electrode. Native gel electrophoresis followed by activity staining was carried out as described below. Protein assays were performed according to the method of Bradford (Bradford. *Anal. Biochem.* 72:248 [1976]).

Analytical gels

Analytical electrophoresis was performed in 0.5 mm thick vertical gels. Composition of the gel was as follows. Running gel: 15% acrylamide, 0.325% bisacrylamide, or 10% acrylamide, 0.22% bisacrylamide, plus 0.375 M Tris, pH 7.0, 0.1% ammonium persulfate, and 7 μl TEMED per 30 ml gel mix. Stacking gel: 4% acrylamide, 0.13% bisacrylamide, 0.125 M bis Tris, pH 7.0, 0.1% ammonium persulfate, and 10 μl TEMED per 30 ml stacking gel mix. The electrode buffer was 25 mM Tris, 0.19 M glycine, pH 8.3. Lysates were diluted with an equal volume of sample buffer (10 mM Tris, pH 7.5, 50% glycerol, 0.01% bromophenol blue) and loaded onto the gels, which were run overnight at 4° C., 8 mamps constant current, toward the anode.

Enzyme Detection

Following electrophoresis, the gels were soaked for 3 minutes in a 1 mM cofactor [NAD(P) or NAD(P)H] solution. Reductive stain reagents were made up in 0.2 M Bis Tris, pH 7.0. oxidative stain reagents were made up in 0.2 M Tris, pH 9.0 immediately before use. The gels were then rinsed quickly in water to remove any cofactor from the gel surface and placed on an ultraviolet light box (Chromato-Vue Transilluminator, Model TL-33, Ultraviolet Products, Inc., San Grabriel, Calif.). After a few minutes, any non-substrate dependent oxido-reductases were visible. Appropriate lanes of the gel were then overlaid with filter paper (Whatman #1) strips soaked in 0.1 M substrate (2-KLG. 5-KDG, 2,5-DKG, 2-KDG, L-idonate, D-gluconate). After 0.1.10 minutes, depending on enzyme level, the substrate dependent bands became visible. Photographs were taken for permanent records at each stage of the staining (Polaroid MP-4 Land Camera with type 667 Polaroid film).

B.3 Cloning of 2-ketoaldonate reductase

The availability of 2-ketoaldonate reductase in *E.herbicola* provides a means for cloning and expression of the gene for the reductase enzyme. The general procedure by which this is accomplished is summarized as follows, and a specific example of such procedures is outlined herein below in Example 7.

The gene encoding 2-ketoaldonate reductase is cloned in either plasmid or phage vehicles from a genomic library created by partially digesting high molecular weight DNA from Erwinia herbicola or other suitable source using a restriction enzyme. For 2-ketoaldonate reductase, a suitable restriction enzyme is Sau 3A. Alternatively, a limited digest with a restriction enzyme having greater specificity, such as SalI, SohI, EcoRI and HindIII may be used. The restriction digest is then ligated either to plasmid vectors replicable in suitable bacterial hosts, or to phage sequences capable of propagation in convenient bacterial cultures. The resulting plasmid or phage libraries are then screened using appropriate techniques, for example, the observation of a color change when plated on 2KDG MacConkey indicator plates or colony growth on minimal 2KDG media plates, or hybridization to DNA probes that are based on the protein sequence of 2-ketoaldonate reductase. Upon recovery of colonies or phage successful in hybridizing with the oligonucleotides provided as probes, identity of the sequence with the desired gene is confirmed by direct sequencing of the DNA and by in vivo expression to yield the desired enzyme

B.4 Expression of 2,5-DKG-Reductase

The complete functional gene encoding 2,5-DKG reductase (see European Patent Application No. 84304277.1) is ligated into a suitable expression vector containing a promoter and ribosome binding site operable in the host cell into which the coding sequence will be transformed. In the current state of the art, there are a number of promotion/control systems and suitable prokaryotic hosts available which are appropriate to the present invention. Similar hosts can be used both for cloning and for expression since prokaryotes are, in general, preferred for cloning of DNA sequences, and the method of 2-KLG production is most conveniently associated with such microbial systems. *E. coli* K12 strain 294 (ATCC No. 31446) is particularly useful as a cloning host. Other microbial strains which may be used include *E. coli* strains such as *E. coli* B, *E. coli* X1776 (ATCG No. 31537) and *E. coli* DH-1 (ATCC No. 33849). For expression, the aforementioned strains, as well as *E. coli* W3110 (F−, λ−, prototrophic, ATCC No. 27325), bacilli such as *Bacillus subtilus,* and other enterobacteriaceae such as *Salmonella typhimurium* or *Serratia marcesans,* and various Pseudomonas species may be used. A particularly preferred group of hosts includes those cultures which are capable of converting glucose or other commonly available metabolites to 2,5-DKG. Examples of such hosts are generally found among the genera Acetobacter, Gluconobacter, Acetomonas and Erwinia. The taxonomy and nomenclature of these genera are such that the same or similar strains are sometimes given different names. For example, *Acetobacter cerinus* used in the example below is also referred to as *Gluconobacter cerinus.* Examples of particular hosts include, but are not limited to, *Erwinia herbicola* ATCC No. 21998 (also considered an *Acetomonas albosesamae* in U.S. Pat. No. 3,998,697); *Acetobacter (Gluconobacter) oxydans* subspecies *melanogenes* IFO 3292, 3293 ATCC No. 9937; *Acetobacter (Gluconobacter) cerinus* IFO 3263 IFO 3266; *Gluconobacter rubiginosus,* IFO 3244; *Acetobacter Frazum* ATCC No. 21409; *Acetobacter (Acetomonas) suboxydans* subspecies *industrious* ATCC No. 23776.

In general, plasmid expression or cloning vectors or conjugative plasmids containing replication and control sequences which are derived from species compatible with the host cell are used in connection with these hosts. The vector ordinarily carries a replication site, as well as marking sequences which are capable of providing phenotypic selection in transformed cells. For example *E. coli* is typically transformed using pBR322, a plasmid derived from an *E. coli* strain (Bolivar et al., *Gene* 2: 95 (1977)). pBR322 contains genes for ampicillin and tetracycline resistance and thus provides easy means for identifying transformed cells. For use in expression, the pBR322 plasmid, or other microbial plasmid must also contain, or be modified to contain, promoters which can be used by the microbial organism for expression of its own proteins. Those promoters most commonly used in recombinant DNA construction include the β-lactamase (penicillinase) and lactose promoter systems (Chang et al., *Nature,* 275: 615 [1978]; Itakura et al., *Science* 198: 1056 [1977]; Goeddel et al., *Nature* 281 544 [1979]) and a tryptophan (trp) promoter system (Goeddel et al., *Nucleic Acids Res.,* 8: 4057 [1980]; EPO Application No. 0036776). While these are the most commonly used, other microbial promoters have been discovered and utilized, and details concerning their nucleotide sequences have been published, enabling a skilled worker to ligate them functionally in operable relationship to genes in transformation vectors (Siebenlist et al., *Cell* 20: 269 [1980]).

By suitable cleavage and ligation DNA sequences encoding 2,5-DKG reductase can be included in the aforementioned vectors prepared as outlined above. Any unnecessary or inhibitory sequences may be deleted and the prokaryotic enzyme may then be purified; or the intact or broken cells used directly as catalysts; or alternatively, the host may be chosen so that once transformed it is capable of effecting the entire conversion of glucose or other suitable metabolite to the desired 2-KLG product.

B.5 Conversion of Glucose or Other Metabolite to 2-KLG by a Single Recombinant Organism The availability of recombinant techniques to effect expression of enzymes in foreign hosts permits the achievement of the aspect of the invention which envisions production of 2-KLG in a single host organism from a readily available metabolite. This method has considerable advantage over presently used methods in that a single viable organism fermentation is substituted for two fermentations, and there is at least a partial balance of the oxidizing and reducing equivalents required for this conversion. At present there is no naturally occurring organism which is known to be capable of catalysis of this entire sequence of steps such that 2-KLG is produced in usable quantities. Certain wild type organisms may produce 2-KLG however the level produced is not sufficient to be economically practical. It has been observed that wild type *A. cerinus* (ATCC 39140) has its own cytoplasmic 2,5 DKG reductase enabling the organism to convert glucose to 2-KLG at a level of approximately 0.2 g/l under controlled conditions. Under the same controlled conditions and using the method of this invention a plasmid capable of expressing 2,5 DKG reductase can be transferred to *A. cerinus* (ATCC 39140) using the process of conjugation, enabling the recipient *A. cerinus* to produce 2-KLG from glucose at a level of 4.5 g/l.

Organisms are known, however, which effect the conversion of glucose or other ordinary metabolic substrate, such as, for example, galactose or fructose into 2,5-DKG. Another group of organisms is known which effects the conversion of the 2,5-DKG into 2-KLG, the latter conversion, of course, being catalyzed by a single enzyme within that organism, but utilizing the power of that organism to supply reducing equivalents.

One approach to producing a single organism conversion that is included in this invention comprises construction of an expression vector for 2,5-DKG reductase as outlined above, and transfer of this vector by any of the gene transfer methods mentioned above such as transformation, transduction or conjugation, into cells which are capable of the initial conversion of ordinary metabolites into the 2,5-DKG substrate for this enzyme. The details of the vector construction, gene transfer, and use of the resultant organism are described in the specification.

An alternative approach is to clone the genes encoding the enzymes known to effect the conversion of glucose or other ordinary metabolite to 2,5-DKG from the organisms known to contain them, to construct expression vectors containing these cloned gene sequences, and to transfer such vectors to cells which normally produce the 2,5-DKG reductase. Examples of the enzymes effecting the conversion of an ordinary metabolite to 2,5-DKG are D-glucose dehydrogenase (Adachi, O. et al., *Agric. Biol. Chem.*, 44(2):301–308 [1980] Ameyama, M. et al., *Agric. Biol. Chem.* 454]:851–861 [1981]), D-gluconate dehydrogenase (McIntire, W. et al., *Biochem. J.*, 231:651–654 [1985]; Shinagawa, E. et al., *Agric. Biol. Chem.* 40[3]:475–483 [1976]; Shinagawa, E. et al., *Agric. Biol. Chem.* 42[5]:1055–1057 [1978]), 5-keto-D-gluconate dehydrogenase and 2-keto-D-gluconate dehydrogenase (Shinagawa, E. et al., *Agric. Biol. Chem.*, 45(5):1079–1085 [1981]). A third approach is to transfer to a neutral host the entire sequence of enzymes comprising the conversion of an ordinary metabolite to 2-KLG. This last approach offers the advantage of choice of host organism almost at will, for whatever desirable growth characteristics and nutritional requirements it may have. Thus, the use as host cells of organisms which have the heritage of a reasonable history of experience in their culture and growth, such as *E. coli* and Bacillus confers the advantage of uniformity with other procedures involving bacterial production of enzymes or substrates.

Once the organism capable of carrying out the conversion has been created, the process of the invention may be carried out in a variety of ways depending on the nature of the construction of the expression vectors for the recombinant enzymes and upon the growth characteristics of the host. Typically, the host organism will be grown under conditions which are favorable to production of large quantities of cells. When a large number of cells has accumulated, the promoter(s) supplied with the recombinant gene sequences either become or are already active, permitting the transcription and translation of the coding sequences. Upon suitable expression of these genes, and hence the presence of the desired catalytic quantities of enzyme, the starting material, such as glucose, is added to the medium at a level of 1.500 g/L and the culture maintained at 20° C. to about 40° C., preferably around 25°–37° C. for 1–300 hours until conversion to 2-KLG is effected. The starting material concentration may be maintained at a constant level through appropriate feed control, and the 2-KLG produced is recovered from the medium either batchwise or continuously by means known in the art.

C. General Methods Employed in the Invention

In the examples below, the following general procedures were used in connection with probe construction, screening, hybridization of probe to desired material and in vector construction.

C.1 Probe Preparation

Synthetic DNA probes were prepared by the method of Crea, R. and Horn, T., *Nucleic Acids Res.*. 8: 2231 (1980) except that 2,4,6-triisopropylbenzenesulfonyl-3-nitro-1,2,4-triazole (TPS-NT) was used as coupling agent (de Rooij, J. et al., *Rec. Trav. Chim. Pays-Bas*, 98: 537 [1979]).

C.2 Isolation of Plasmids. Cleavage with Restriction Enzymes

Plasmids were isolated from the identified cultures using the cleared lysate method of Clewell, D. B. and Helinski, *Biochemistry* 9: 4428 (1970), incorporated herein by reference, and purified by column chromatography on Biorad A-50 Agarose. Smaller amounts (minipreps) were prepared using the procedure of Birnboim, H.C. *Nucleic Acids Research* 7: 1513 (1979).

Fragments of the cloned plasmids were prepared for sequencing by treating about 20 μg of plasmid with 10 to 50 units of the appropriate restriction enzyme or sequence of restriction enzymes in approximately 600 μl solution containing the appropriate buffer for the restriction enzyme used or sequence of buffers; each enzyme incubation was at 37° C. for one hour. After incubation with each enzyme, protein was removed and nucleic acids recovered by phenol-chloroform extraction and ethanol precipitation. Alternatively, plasmids were fragmented by DNAase I digestion in the presence of $MnCl_2$ (Anderson, S., *Nucleic Acids Res.* 9, 3015 [1981]) or by sonication (Deininger, P. L., *Analyt. Biochem.* 129, 216 [1983]). After cleavage, the preparation was treated for one hour at 37° C. with 10 units Klenow DNA polymerase or T4 DNA polymerase in 100 μl of Klenow buffer (50mM KPi, pH 7.5. 7mM $MgCl_2$, lmM BME), containing 50 nmol dNTP. Protein was removed and nucleic acids recovered as above, and the nucleic acids suspended in 40 μl of loading buffer for loading onto 6 percent polyacrylamide gel, as described above for sizing. (Alternatively, fragments may be cloned directly into an M13 vector.)

DNA sequencing was performed by the dideoxynucleotide chain termination method (Sanger, F. et al.

*Proc. Natl. Acad. Sci. USA* 74, 5463 (1977)) after cloning the fragments in an M13-derived vector (Messing et al. *Nucleic Acids Res.* 9, 309 (1981)).

C.3 Ligation Procedures

DNA fragments, including cleaved expression plasmids were ligated by mixing the desired components (e.g. vector fragment cut from 0.25 μg plasmid is mixed with insert cut from 1 μg of plasmid in 20 μl reaction mixture). which components were suitably end tailored to provide correct matching, with T4 DNA ligase. Approximately 10 units ligase were required for μg quantities of vector and insert components. The resulting plasmid vectors were then cloned by transforming *E. coli* K12 strain 294 (ATCC 31446) or DH-1 (ATCC 33849). The transformation and cloning, and selection of transformed colonies, were carried out as described below. Presence of the desired sequence was confirmed by isolation of the plasmids from selected colonies, and DNA sequencing as described below.

The following examples serve to illustrate but not to limit the invention:

EXAMPLE 1

Recombinant 2,5-DKG Reductase

A. Construction of Expression Vectors for 2,5-DKG Reductase

The 2,5-DKG reductase gene, accompanied by either its own or a synthetic ribosome binding site, is inserted 'downstream' of the *E. coli* trP (or tac) promoter or the pACYC184 CAT promoter on expression plasmids which also contain a tetracycline resistance gene or other selectable marker, and an origin of replication derived from plasmids ColE1, 15A, or RSF1010. Some constructs may contain, in addition, an active gene coding for *E. coli* trp repressor or the *E. coli* lac repressor which allows the expression of the 2,5-DKG reductase gene to be regulated by exogenously added indole acrylic acid or isopropylthio-β-galactoside (IPTG), respectively. Various mutated versions of the above plasmids are also employed for the expression of 2,5-DKG reductase.

A cloned 2.2 Kb BamHI fragment of Corynebacterium sp (ATCC 31090) DNA, containing a portion of the 2,5-DKG reductase gene. was isolated with the 43-mer probes. An 0.12 Kb PstI/BamHI fragment of this plasmid was further used as a probe to isolate an overlapping 0.88 Kb PstI fragment of Corynebacterium so DNA, which contained the rest of the gene. pDKGR2, as described in U.S. Pat. No. 4,757,012 issued July 12, 1988, which is hereby incorporated by reference, (containing the 2.2 Kb BamHI fragment) was digested with NcoI, treated with *E. coli* DNA polymerase I Klenow fragment and dNTPs to create flush-ended DNA, then further digested with BamHI to release an 0.87 Kb fragment; this fragment was purified by electrophoresis on low-melting-point agarose. The plasmid pDKGR9 (containing the 0.88 Kb PstI fragment) was digested with PstI and BamHI, and the resultant 0.76 Kb fragment similarly isolated on low-melting-point agarose. The 0.87 Kb NcoI/BamHI fragment and the 0.76 Kb BamHI/PstI fragment were then combined with SmaI/PstI-digested M13mp9 and ligated to yield an M13 recombinant ("mit12") with a 1.6 Kb insert of Corynebacterium sp DNA containing the entire 2,5-DKG reductase gene.

To mit12 single-stranded DNA a "deletion primer" (sequence: ACGGCCAGTGAATTCTAT-GACAGTTCCCAGC) and AluI fragments of M13mp9 DNA were annealed. This template-primer combination was then treated with *E. coli* DNA polymerase Klenow fragment in the presence of dNTPs and T4 DNA ligase to create in vitro heteroduplex mit12 RF molecules, as described by Adelman et al., DNA 2: 183 (1983). These molecules were used to transform the host JM101 (Messing, *J. Recomb. DNA Tech. Bull.* 2:43 [1979]). and recombinant phage incorporating the desired deletion were detected by plaque hybridization using the deletion primer as a probe (Adelman et al., *DNA* 2:183 [1983]). This construction was designated mit12Δ.

Figure 7:
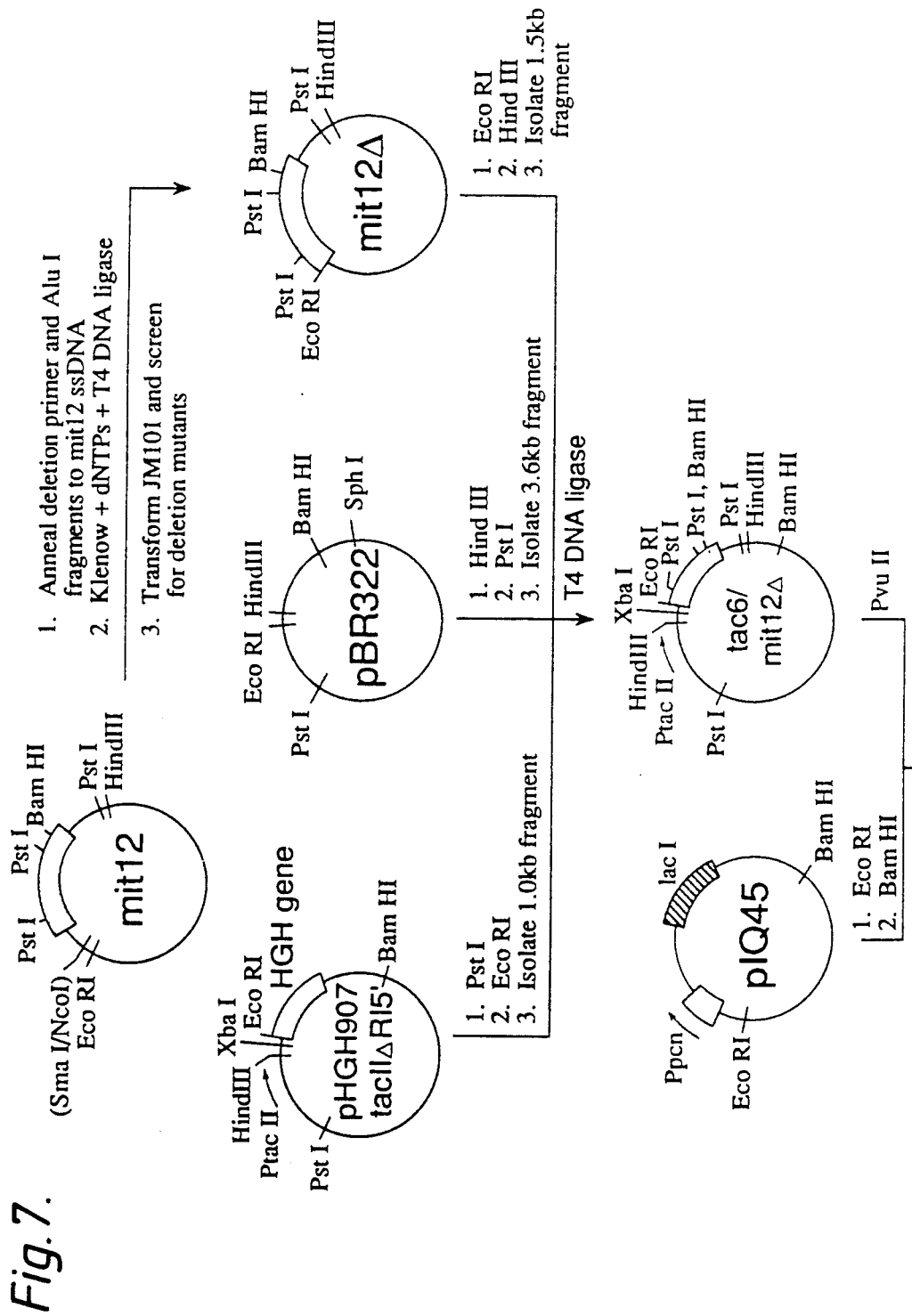
FIG. 7 shows the construction of the expression vector p269 for 2,5-DKG reductase.
Figure 7:
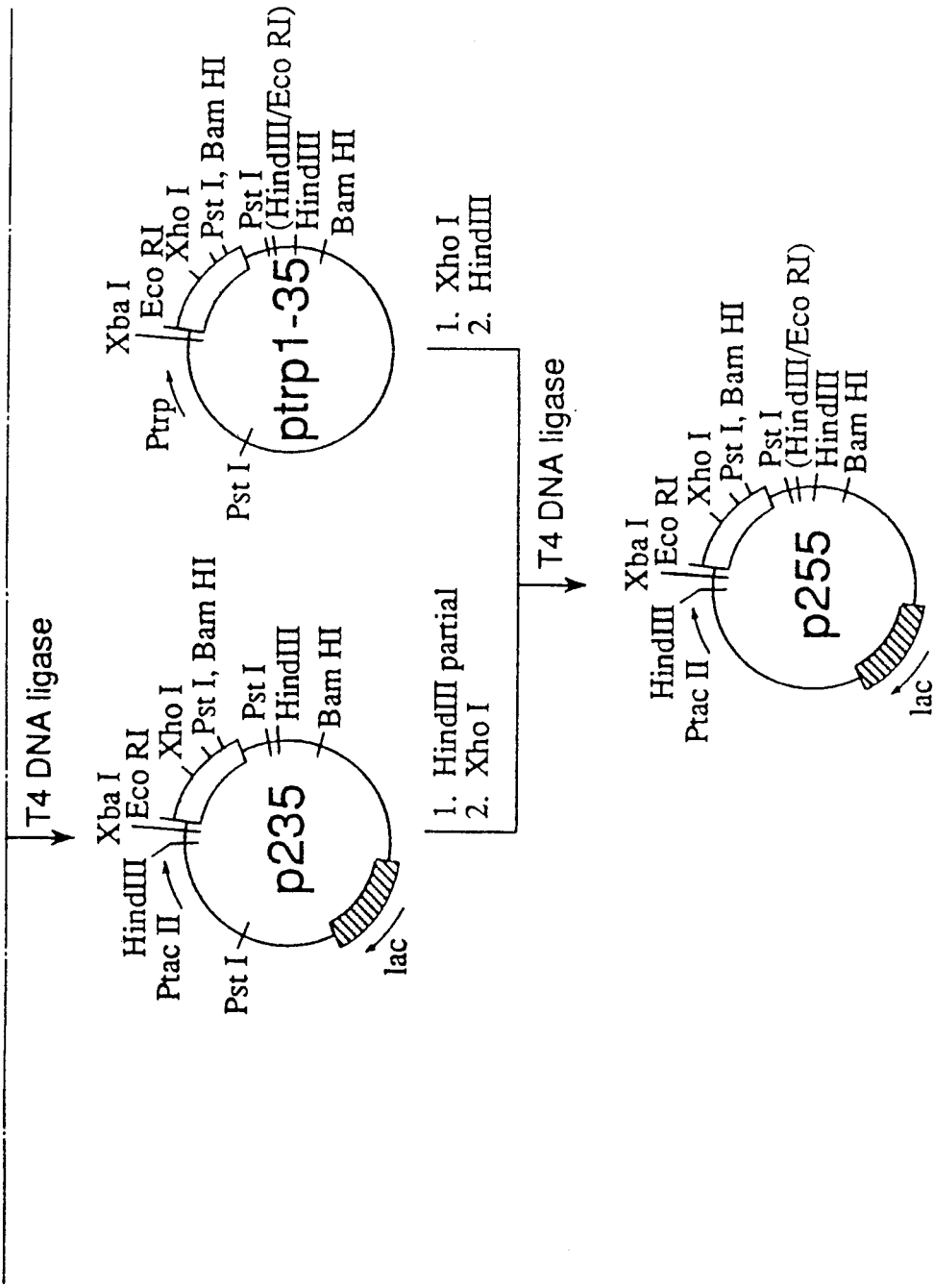

The mit1266 RF DNA was digested with EcoRI and HindIII to yield a 1.5 Kb fragment containing the 2,5-DKG reductase gene. The human growth hormone expression plasmid, pHGH207-lptrpΔRI5′ (pHGH207-lptrpΔRI5′ is a derivative of pHGH207.1 [de Boer et al., *Proc Natl. Acad. Sci. USA* 80: 21 (1983)] in which the EcoRI site between the ampicillin resistance gene and the trp promoter has been deleted), was digested with EcoRI and PstI to yield a 1.0 Kb fragment containing the *E. coli* trp promoter. Alternatively, the human growth hormone expression plasmid, pHGH907tacII-ΔRI5′ (pHGH907tacIIΔRI5′ is a derivative of pHGH907tacII, [de Boer et al., Id.] in which the EcoRI site between the ampicillin resistance and the tacII promoter has been deleted) was digested with EcoRI and PstI to yield a 1.0 kb fragment containing the tacII promoter. pBR322 was digested with PstI and HindIII to yield a 3.6 Kb fragment. The three fragments in each case, either with the trp or tac promoter, were ligated together to form an expression plasmid for 2,5-DKG reductase, designated pmit12Δ/trpl or pmit12Δ/tac6 (FIG. 7). The plasmid pmit12Δ/tac6 was then treated to provide it with its own copy of the *E. coli* lac repressor gene so that expression of the 2,5-DKG reductase gene from the tacII promoter would be regulatable by lactose or its analogues (e.g., IPTG [isopropyl-β-D-thiogalactoside]) in a variety of hosts. Briefly, a 1.1 kb EcoRI/BamHI fragment, containing the *E. coli* lac repressor gene under the control of the *B. licheniformis* penicillinase promoter and ribosome binding site, was isolated from plasmid pIQ45 (Yansura and Henner, *Proc. Natl. Acad. Sci. USA* 81:439 [1984]), treated with *E. coli* DNA polymerase I Klenow fragment and dNTPs to produce blunt ends, and ligated into the PvuII site of pmit12Δ/tac6, resulting in a plasmid termed p235 (FIG. 7). In order to restore the promoter for the tetracycline resistance gene on plasmid p235 it was digested with XhoI and HindIII (partial) to release a 6.2 kb fragment and this was ligated to a 1.2 kb XhoI/HindIII fragment from plasmid ptrp 1.35 (see U.S. Pat. No. 4,757,012, issued July 12, 1988) containing the 3′-portion of the 2,5-DKG reductase gene and the "upstream" sequences (e.g., -35 box) for the pBR322 tetracycline resistance gene promoter (FIG. 7). This final plasmid was termed p255 (*E. coli* hosts) or p269 (*Erwinia herbicola* hosts).

B. Transformation of *Erwinia herbicola* with an Expression Vector for 2,5 DKG reductase Cells are prepared for transformation by the method of Lacy and Sparks, *Phytopathological Society*, 69: 1293.1297 (1979). Briefly a loop of suitable host cells, *Erwinia herbicola* (ATCC 21998). or *E. coli* MM294 (ATCC 31446), is inoculated into 5 ml of LB medium and incubated at 30° C. for 14–16 hrs. A 1:100 dilution of this overnight growth is inoculated into LB, the culture grown to OD$_{590}$ of 0.4, and the cells recovered by centrifugation at 4° C. The pellet was resuspended in 1/3 volume of 10 mM NaCl, again centrifuged at 4° C., the pellet resuspended in an equal volume of 30 mM CaC$_2$, and after 60 minutes at 0° C., the cells again centrifuged at 4° C. The pellet is resuspended in 1/12 volume of 30 mM CaCl$_2$ and stored at 4° C. overnight. (Alternatively, cells may be resuspended in 30 mM CaCl$_2$, 15 percent glycerol, and stored at −70° C.)

Transformation is effected by incubation of 1 μg plasmid, p269, in 0.2 ml of competent cells at 0° C. for 2 hr followed by heating to 42° C. for 1 min. 3 ml of LB broth is added and cells are allowed to recover for 4 hrs at 37° C., then cells are plated on selective medium as described by Lacy and Sparks (supra).

EXAMPLE 2

L-idonic Acid in *E. herbicola* ptrpl-35 Fermentations

The bioconversion of D-glucose to 2-KLG as carried out by *Erwinia herbicola* 21998 ptrp 1-35 (U.S. Pat. No. 4,757,012) is shown in FIG. 1. A 30 g/l shot of D-glucose is rapidly and efficiently oxidized via the desired metabolic pathway comprising its conversion to D-gluconate (GA) to 2-keto-D-gluconate (2-KDG) which in turn is converted to 2,5-diketo-D-gluconate (2,5-DKG). This is followed by a slower and somewhat less efficient reduction of 2,5-DKG to 2-KLG, which is catalyzed by the recombinant expression plasmid encoding 2,5-DKG reductase. In addition to production of the desired metabolites, a previously unknown metabolite was observed. This unknown metabolite was observed as a significant HPLC peak eluting on an ion exchange column with a retention time in the aldonic acid region (Lazarus and Seymour, supra). Furthermore, this unknown metabolite disappeared as 2-KLG appeared, in the absence of any other carbon source, suggesting that the two compounds are structurally related. The metabolite was identified as L-idonate based on: a) identical observed retention times on both the ion exchange and organic acids HPLC systems; and b) identical retention times and mass spectra of the pertrimethylsilated derivative of the unknown peak as compared with a standard of authentic L-idonic acid as measured by gas chromatography mass spectrometry. The identification of idonate and subsequent quantitation in fermentations allowed a complete closure of the carbon balance of the reaction.

EXAMPLE 3

Metabolism of L-Idonic Acid

The metabolic pathways involved in the synthesis and degradation of IA were studied in *E. herbicola* ptrpl.35. L-idonate is a natural product and has been identified as an intermediate in L-(+)- tartaric acid biosynthesis from L-ascorbate in grapes (Saito and Kasai, *Plant Physiol.* 76:170 [1984]) and as a sorbitol catabolite in a number of species from the genera Gluconobacter, Acetobacter, or Pseudomonas (Makeover et al , *Biotech and Bioeng.* 17:1485 [1975]). Both of these routes are thought to involve oxidation of L-idose to produce IA.

Although a large number of potential metabolic routes from glucose exist, IA is likely produced from either 2-KLG or 5-keto-D-gluconate (5-KDG) catalyzed by a stereospecific pyridine nucleotide-linked reductase. Evidence for both the 5-KDG route in Fusarium species (Takagi, *Agric. Biol. Chem.* 26:719 [1962]) and the 2-KLG route in a variety of microorganisms has been observed (Makeover et al., supra). Shake flask incubations of whole cells of *E. herbicola* at 11 OD$_{550}$ containing 12 g/l of either 2-KLG or 5-KDG were carried out. Approximately 4 g/l of IA was produced in flasks containing 2-KLG in 40 hours. The total IA and 2-KLG concentration remained constant throughout the bioconversion. No metabolites were observed in flasks containing 5-KDG which was eliminated by 17 hours. Furthermore, *E. herbicola* was grown using either 5-KDG, G, GA, 2-KDG, or 2,5-DKG as the sole carbon source in minimal media. *E. herbicola* did not grow when either 2-KLG or IA was used. Thus the IA produced in *E. herbicola* into which an expression vector encoding 2,5-DKG reductase has been transferred is derived from 2-KLG catabolism.

EXAMPLE 4

Reductive and Oxidative Enzymatic Pathways

*E. herbicola*

The metabolic pathways in the metabolism of D-glucose to 2-KLG in *E. herbicola* ptrpl-35 or *E. herbicola* p269 were studied. The metabolic diversion via a secondary metabolic pathway of 2-KLG to IA in fermentations of *E. herbicola* was discovered for the first time since neither of these carbohydrates was known to be a natural product in this strain. Since 2-KLG appears to be produced from IA oxidation (FIG. 1), 2-KLG may be produced via a reversible reduction or a separate oxidative pathway.

The metabolism of carbohydrates by ketogenic bacteria has been investigated in a wide variety of strains (Asai, *Acetic Acid Bacteria* [Univ. Park Press. Baltimore, Md., 1968]). The enzymes involved in the specific reactions involving glucose and its metabolites have been characterized primarily by Ameyama, *Methods in Enzymology* 89:187–210 (1982), Lessie and Phibbs, *Ann. Rev. Microbiol.* 38:359 (1984) and their coworkers. Oxidation of glucose to ketogluconates has been shown to proceed via membrane bound dehydrogenases that are linked to the electron transport chain. Subsequent reduction of the ketogluconates or their phosphorylated forms is catalyzed by cytosolic NAD(P)H requiring reductases to products that can enter into central metabolism.

Reversible NAD(P)H linked reductases for 2-KLG, 2-KDG, 2,5-DKG, and 5-KDG were found to be present in the cytosol of *E. herbicola* by activity assays of crude lysates. The activities were separated on a DEAE-cellulose column using a linear salt gradient (FIG. 2). The 5-KDG reductase required NADPH and stereospecifically reduced 5-keto-D-gludonate (5-KDG) to D-gluconate (GA) as measured by HPLC and GCMS (Lazarus and Seymour, supra). A second peak of activity eluted at 0.33 M NaCl, which catalyzed the stereospecific reduction of 2-keto-L-gulonate (2-KLG) to L-idonate (IA), 2-KDG to GA, and 2,5-DKG to 5-KDG, using either NADPH or NADH as the coenzyme, the former being preferred. This enzyme, named 2-ketoaldonate reductase (2-KR) due to its lack of substrate specificity, has been further purified and characterized. The enzyme is referred to as 2-KR(A) since it was the first 2-ketoaldonate reductase purified. It is encoded by the tkrA gene. The last peak of activity is the 2-KLG producing recombinant 2,5-DKG reductase expressed from the cloned Corynebacterium sp gene (Anderson et al., Science 230:144 [1985]). An investigation to identify 2-ketoaldonate kinases, such as those observed in the Pseudomonads (Lessie and Phibbs, supra.), has been carried out, however no evidence has been obtained that would support the existence of these metabolic pathways. However, it is possible that these enzymes exist based on the fact that 6-phosphogluconate is a better substrate than gluconate for the reduction of NADP+ at pH 9.0.

The broad specificity observed for this 2-ketoaldonate reductase is similar to the nonspecificity of other 2-keto-D-gluconate reductases purified from a number of ketogenic bacteria (Ameyama and Adachi, *Methods in Enzymology* 89:203 [1982]). It has been postulated that these reductases are present in order to utilize the oxidized carbohydrates for the production of gluconate, which can enter into central metabolism, and also to regenerate NADP+. The minimum requirements for substrate activity for 2-ketoaldonate reductase include a carboxylate moiety at C1, a keto group at C2, and a hydroxyl group at C3, since hydroxypyruvate, but not pyruvate also shows activity. The stereochemistry at the epimeric C3 would seem to indicate that the S-configuration may also be required. The products of the reduction reaction all possess the R-epimeric configuration at C2, consistent with the idea that the different keto-substrates are all bound to the enzyme in an identical manner and that the stereochemical transfer of hydrogen from NAD(P)H is conserved.

The carbohydrate oxidizing enzymes in *E. herbicola* were found to be membrane dehydrogenases. Their membrane location is based on the fact that a) the activities spin down with the membrane fraction in an ultracentrifuge; b) the activities are solubilized by a variety of detergents; and c) artificial electron acceptors such as 2,6-dichloroindophenol or $O_2$ coupled to phenazone methosulfate are reduced whereas neither NAD+ nor NADP+ serve as electron acceptors. Activities as measured with either an $O_2$ electrode or spectrophotometrically give comparable results. Thus, activities for glucose (G), D-gluconate (GA), 2-keto-D-gluconate (2-KDG), and most interestingly, L-idonate (IA) dehydrogenases have been identified. These enzymes are most likely heme and flavin containing proteins linked to the cytochrome chain (Ameyama et al., *Agric. Biol. Chem.* 51:2943 [1987]). The product of the idonate dehydrogenase catalyzed reaction with IA was found to be 2-KLG as measured by HPLC and GCMS; 2-KDG, the product of GA oxidation, is further oxidized to 2,5-DKG.

EXAMPLE 5

Reduction and Oxidation Enzymatic Pathways in *A. Cerinus*

The metabolic pathways in the metabolism of D-glucose to 2-KLG in *A. cerinus* ATCC 39140, another 2,5 DKG producing strain, have also been studied. In this strain both 2-KLG and IA are natural products derived from glucose metabolism as evidenced by HPLC and GC methodology as described above. Reversible NAD(P)H linked reductases for 2-KLG, 2-KDG, 2,5-DKG, and 5-KDG were found to be present in the cytosolic fraction based on activity assays of crude lysates. The activities were separated on a MonoQ anion exchange column (Pharmacia) using a linear salt gradient. Product analysis by HPLC and GC confirmed the presence of an NAD(P)H dependent 2-ketoaldonate reductase that catalyzed the reduction of 2-KLG to IA, 2-KDG to GA, or 2,5 DKG to 5-KDG. Activities for two 5-KDG reductases were also observed The NAD(P)H linked reduction of 5-KDG to GA was catalyzed by 5KR(G) and the NADH linked reduction of 5-KDG to IA was catalyzed by 5KR(I). Additionally, an NADH dependent 2,5 DKG reductase that converted 2,5 DKG to 2-KLG was present. Based on data from activity stained native gels a second NAD(P)H dependent 2-ketoaldonate reductase was also found that has similar substrate and product profiles to the first one.

The carbohydrate oxidizing enzymes were also found to be membrane bound dehydrogenases with similar properties to those observed in *E. herbicola*. Thus activities for the enzymes that catalyze the reaction of G to GA, GA to 2-KDG, 2-KDG to 2,5-DKG and IA to 2-KLG were observed.

The specific activities in the crude membrane fraction for GA (spec. act. = 0.45 μmol/min.mg protein) and IA (spec. act. −0.35 μmol/min.m g protein) oxidation are comparable. However, these appear to be different enzymes based on the fact that each enzyme was specifically inhibited only by its own product, i.e. 2-KLG competitively inhibited ($K_i$=13 mM) idonate dehydrogenase but not gluconate dehydrogenase and 2-KDG competitively inhibited ($K_i$>10 mM) gluconate dehydrogenase but not idonate dehydrogenase. Apparent $K_m$ values of 20 mM for IA and 0.33 mM for GA were observed at pH 6.0, 25° C. for the idonate and gluconate dehydrogenase activities, respectively.

Figure 10:
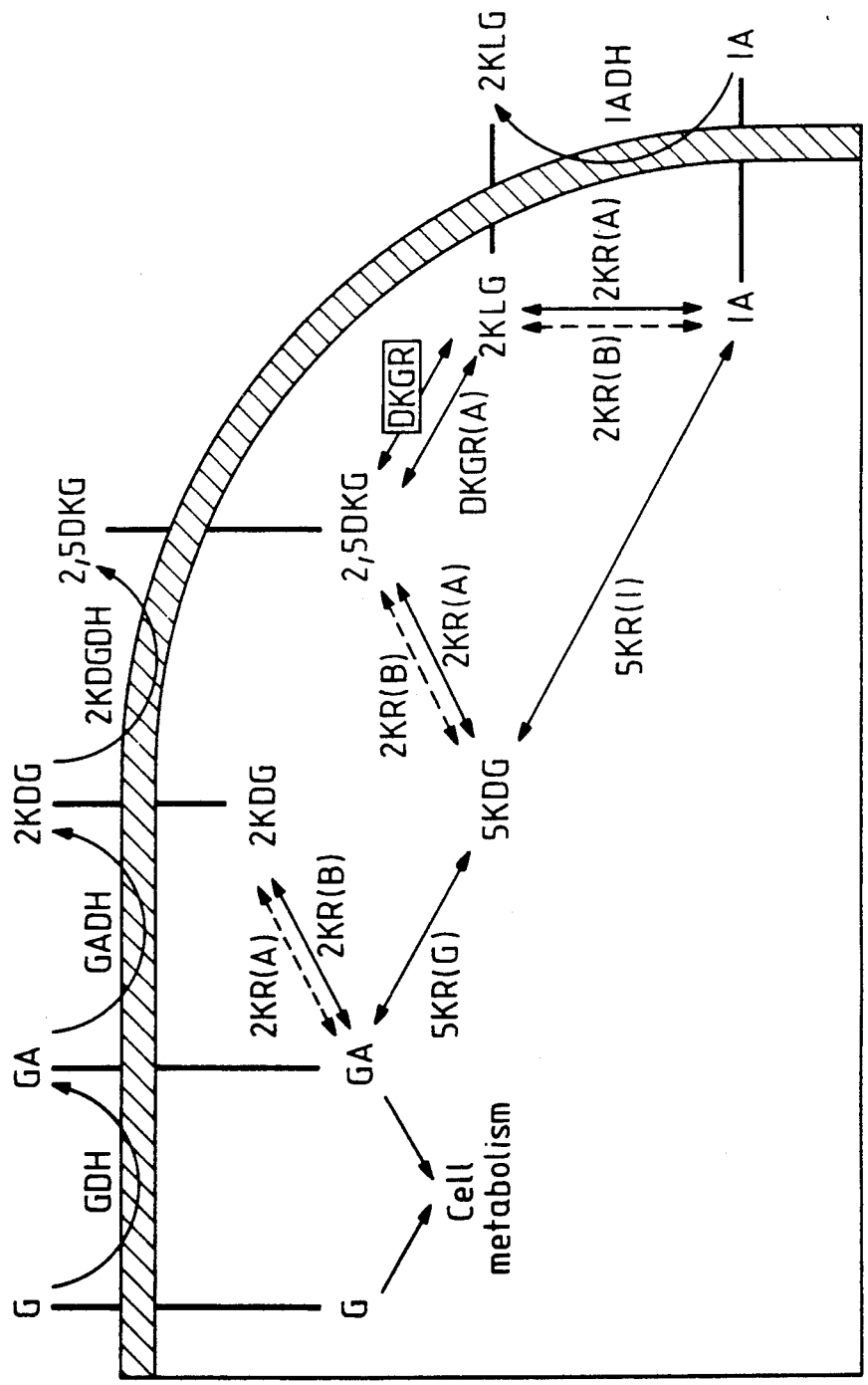
FIG. 10 shows the desired metabolic pathway and secondary metabolites and metabolic pathways in Acetobacter cerinus (ATCC 39140; IFO 3263).

The metabolic pathways involved in carbohydrate metabolism for *A. cerinus* are shown in FIG. 10.

EXAMPLE 6

Controllable Expression of 2,5 DKG-reductase and its Effect on Product Yields

Plasmid p269 was constructed as described above in Example 1 utilizing a regulatable promoter system for 2,5-DKG reductase expression. p269 was shown to produce less reductase when fully induced than the plasmid ptrpl.35, (U.S. Pat. No. 4,575,012 issued July 12. 1988) in shake flask cultures. Production of 2-KLG at the 10L scale using plasmid p269 was compared to production using the constitutive plasmid ptrpl-35 and a non-DKG reductase producing plasmid, pBR322.

A single colony isolate transformed with either p269, ptrpl-or pBR322 was removed from a Luria Broth agar plate, 5 μg/ml tetracycline, and resuspended in 50 ml Luria broth 5 μg/ml tetracycline. The culture was incubated at 30-C until the cell concentration reached approximately 1.0 $A_{550}$. The inoculum was transferred aseptically to a 10L fermentor containing the following ingredients:

| | |
|---|---|
| $(NH_4)_2SO_4$ | 2.5 g/L |
| $KH_2PO_4$ | 3.0 |
| $K_2HPO_4$ | 2.0 |
| $MgSO_4\ 7H_2O$ | 1.0 |
| Ucon Antifoam | 1.0 ml/L |
| q.s. to 9.5 L with Deionized $H_2O$ | |

Sterilized separately and added after fermenter sterilization

Figure 5:
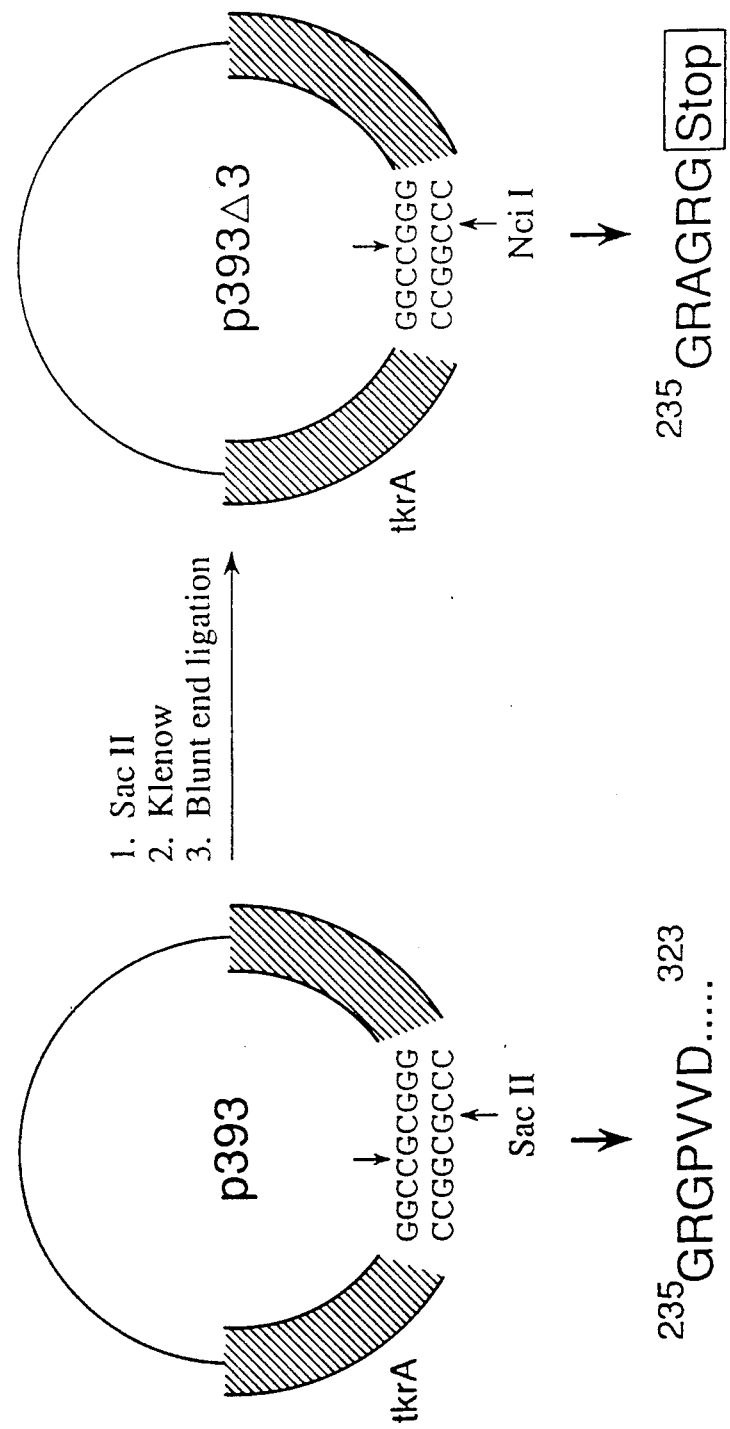
FIG. 5 shows the in vitro deletion mutagenesis of the *E. herbicola* tkrA gene at the SacII site.

| | |
|---|---|
| Glucose | 10 g/L |
| Yeast Extract | 12 g/L | termination 4 amino acid residues downstream from the sacII site (FIG. 5).

Since *E. herbicola* is naturally resistant to ampicillin, p393Δ3 could not be directly transferred into the strain. Therefore, a 1.3 kB pvuI fragment from p393Δ3 was cloned into the pvuI site of pBR322 creating plasmid pBRpvuΔ3. This plasmid was transformed into competent *E. herbicola* selecting for tetracycline resistance.

The tkrAΔ3 deletion was then introduced into the Erwinia chromosome by homologous recombination. Erwinia containing pBRpvuΔ3 was grown in LB broth containing tetracycline to an $A_{660}$ of 0.4 and the cells from 10 ml of culture were pelleted and resuspended in 1 ml sterile 0.01M MgSO4. The bacteria were exposed to 60 J/m$^2$ of UV light from a GE germicidal lamp. The bacteria were then returned to LB tetracycline media and allowed to grow to saturation. The bacteria were then plated on MacConkey agar containing 1% 2-KDG and incubated overnight at 37° C. White colonies appeared at a frequency of approx. 1%. One colony, unable to grow on minimal 2-KDG plates, was designated *E. herbicola* tkrAΔ3. Growth in the absence of tetracycline resulted in the spontaneous loss of the pBRpvuΔ3 plasmid as evidenced by loss of tetracycline resistance. Thus, it appeared that the tkrAΔ3 deletion had been transferred to the chromosomal copy of tkrA by a double reciprocal crossover event (FIG. 6).

EXAMPLE 9

Characterization of the *E. herbicola* tkrAΔ3 Mutant

The introduction of the tkrAΔ3 mutation into the Erwinia chromosome was confirmed from Southern blot data. The functional deletion of the tkrA chromosomal gene was confirmed by in vitro activity assays for 2-ketoaldonate reductase as well as analysis by activity stained native gel electrophoresis. The relative 2-ketoaldonate reductase activities of cell lysates from Luria Broth grown cultures using 2-KLG as the substrate was at least 30-fold lower for the tkrAΔ3 mutant as compared to the wild type. In addition to the phenotypic lack of growth on minimal 2-KDG media, the mutant strain was white on 2-KDG tetrazolium indicator plates in contrast with the parent which gave red colonies (Bochner and Savageau, *Appl. and Env. Microbiol.* 33:434 [1977]), consistent with the idea that the tkrA mutant cannot utilize 2-KDG. Further confirmation of the chromosomal mutation was evident based on complementation experiments. The phenotype of the tkrAΔ3 mutant when transformed with plasmid p544, which expresses the functional tkrA gene as well as kanamycin resistance, returned to that of the parent. Plasmid p544 was a derivative of plasmid p460 wherein the kanamycin resistance gene (Pharmacia) was inserted into the PstI site.

EXAMPLE 10

Bioconversion with the 21998tkrAΔ3 Strain

Figure 8:
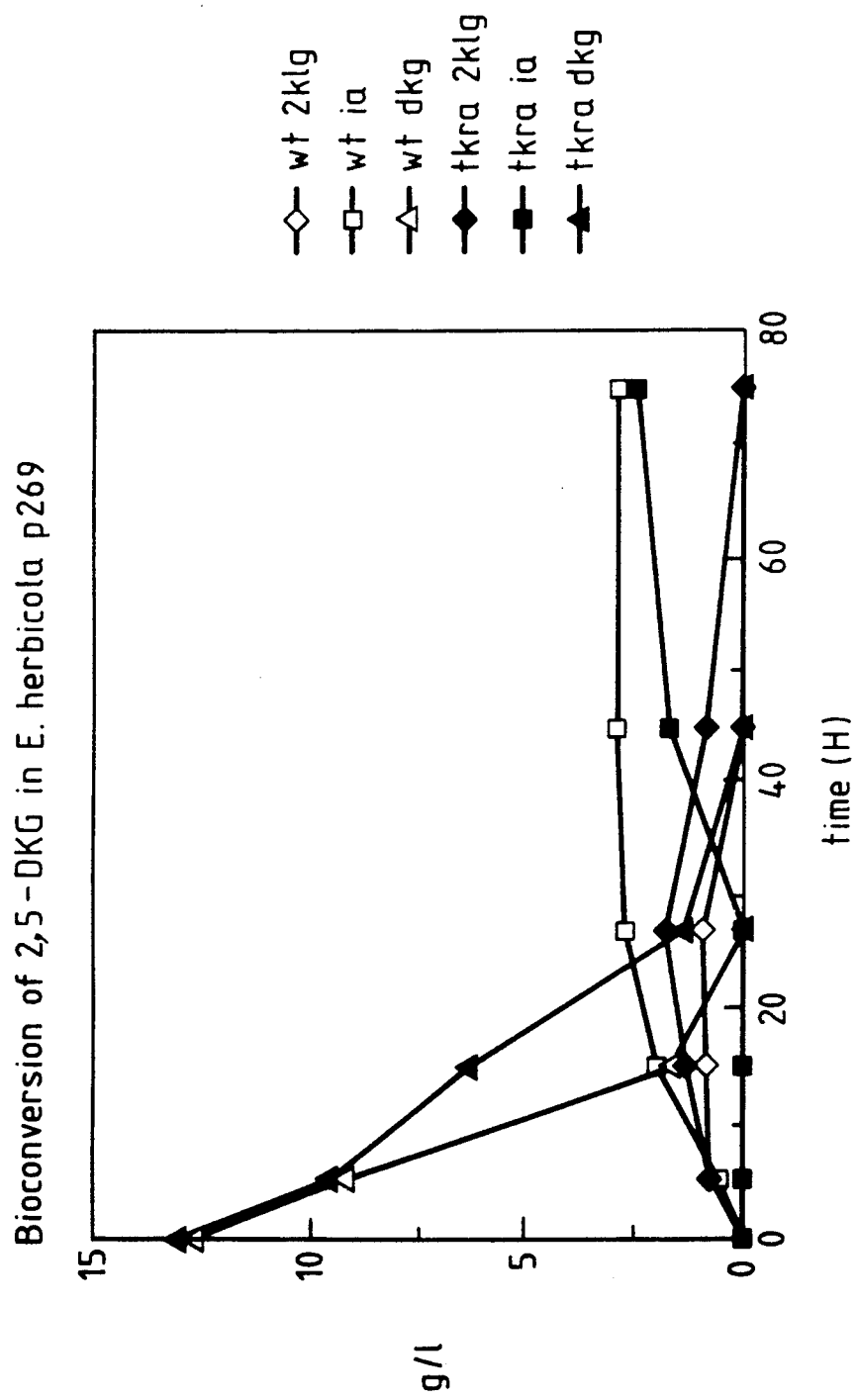
FIG. 8 shows 2,5-DKG bioconversion in *E. herbicola* into which the expression vector for 2 5-DKG reductase was transferred and the tkrA gene was deleted.

An experiment was carried out to show that the deletion of the tkrA gene in fact produced a strain with improved bioconversion characteristics, i.e., the lack of IA production from 2-KLG and the lack of metabolic diversion of 2,5-DKG to 5-KDG. 2,5-DKG was added to both 21998p269 and 21998tkrAΔ3p269 which were grown in LB media with IPTG to induce 2,5-DKG reductase expression. The subsequent bioconversion to 2-KLG is shown in FIG. 8. After 27 hours the tkrAΔ3 mutant strain produced 1.8 g/l of 2-KLG and no IA compared to the parent which produced 0.9 g/l of 2-KLG and 2.7 g/l of IA. However, at the end of the fermentation all of the 2-KLG was converted to IA in both strains.

EXAMPLE 11

Discovery of the tkrB Gene in *E. herbicola*

The fact that idonate was still produced in the tkrA$^-$ mutant led to the discovery of a second 2-ketoaldonate reductase [2KR(B)], encoded by an inducible tkrB gene. This protein can be purified from the tkrAΔ3 strain and the gene has been cloned (see below). Evidence that 2KR(A) and 2KR(B) are in fact different enzymes is based on observed differences in protein sequence, molecular weight on SDS gels, subunit composition, migration on native gels, kinetic parameters, and gene sequence. 2KR(B) activity is inducible in LB media by a variety of carbohydrates which are listed on Table 1. In addition to the effects observed for 2KR(B) induction there appears to be a mechanism involving coordinate regulation of 5-KDG reductase activity as well, suggesting that these genes may be part of an operon and under similar control The 2-ketoreductase activity induced by a number of carbohydrates shown on Table 1 may function in other pathways. 2-keto reductase activity is found widely elsewhere in nature. We have also identified 2-keto aldonate reductase activity in both *E. coli* MM294 and Corynebacterium sp. ATCC 31090, neither of which is known to be ketogenic nor produce 2-KLG as a natural product.

TABLE I

| 2-Keto- and 5-Keto- Reductase Activities in *E. herbicola* 21998tkrAΔ3 | | |
|---|---|---|
| Compound | 2 KR Spec. Act. (μmole/min · mg) | 5 KR Spec. Act. (μmol/min · mg) |
| none | 0.002 | 0.0008 |
| D-glucose | 0.167 | 0.27 |
| D-gluconate | 0.020 | 0.144 |
| 2-KDG | 0.045 | 0.143 |
| 5-KDG | 0.119 | 0.105 |
| 2,5-DKG | 0.122 | 0.103 |
| 2-KLG | 0.014 | 0.061 |
| D-glycerol | 0.024 | 0.035 |
| D-mannitol | 0.027 | 0.032 |
| D-fructose | 0.028 | 0.032 |

Figure 9:
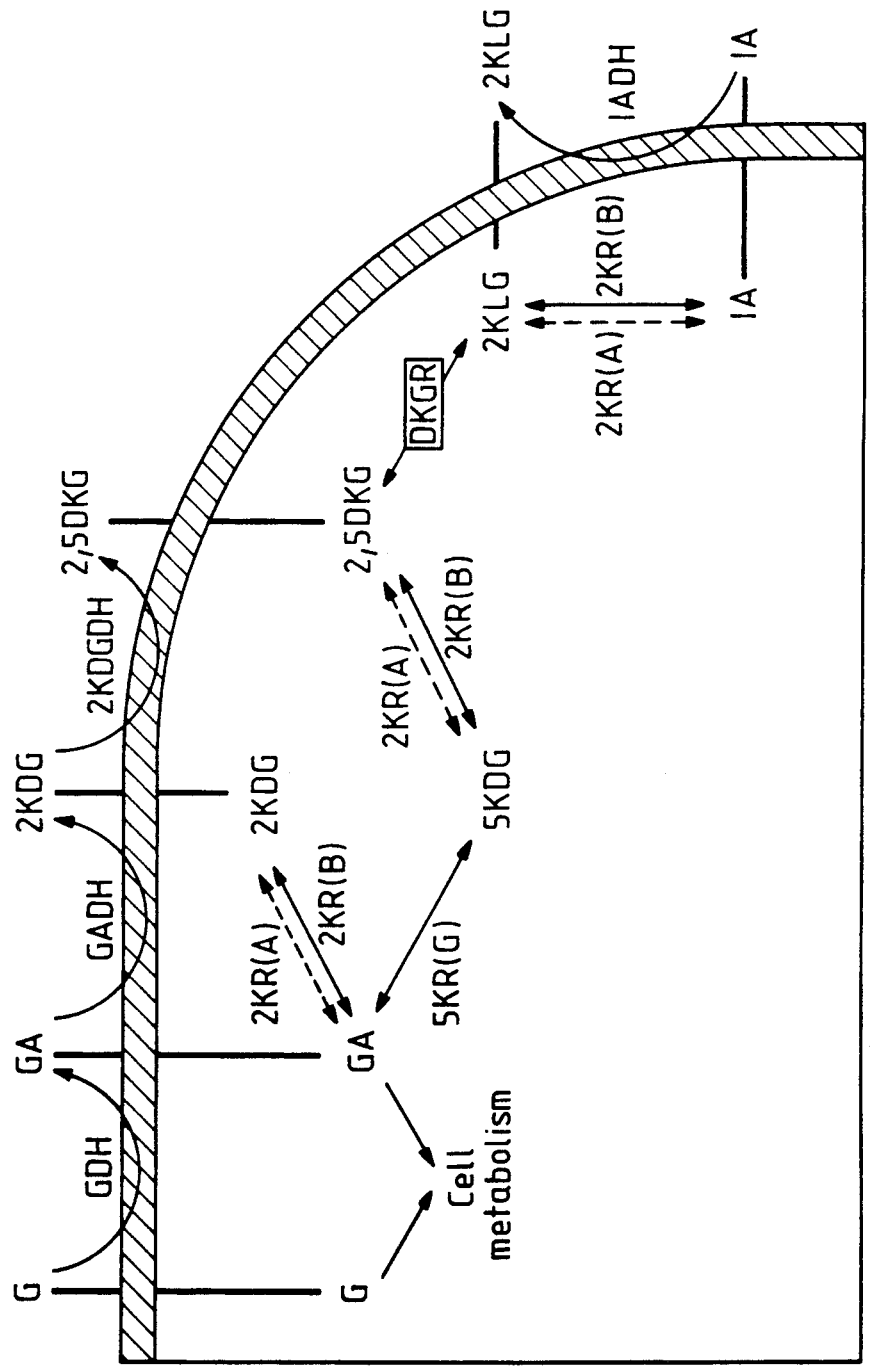
FIG. 9 shows the desired metabolic pathway and secondary metabolites and metabolic pathways in *E. herbicola* (ATCC 21998).

The secondary metabolites and metabolic pathways shown in FIG. 9 describe the carbohydrate metabolism arising from the transfer of genetic material rendering the cell capable of converting glucose to 2-KLG discovered in *Erwinia herbicola*. After the identification of 2KR(A) as the enzyme responsible for IA biosynthesis from 2-KLG, the gene was cloned. The tkr(A) gene was deleted from the chromosome which in turn lead to the discovery of 2KR(B). Fermentations of *E. herbicola* having the secondary metabolites and metabolic pathways eliminated demonstrate that under certain conditions the metabolic diversion of 2-KLG to IA can be blocked. In addition the metabolic diversion of 2,5-DKG to 5-KDG can be blocked by the same deletion. This is one of the first demonstrations of genetic manipulation of secondary metabolites or metabolic pathways for strain development in a microorganism to which genetic material has been transferred. With the advent of rDNA technology we now have been able to alter the basic metabolism of microorganisms to produce small molecules not only by the genetic insertion of new

| | |
|---|---|
| Tetracycline HCl | 5 mg/L |
| IPTG (Inducer) | 1.2 g/L | pH is adjusted at 6.0+/− 0.1 with $H_3PO_4$ and $Na_2CO_3$ prior to inoculation and controlled at 6.0 throughout the fermentation. The temperature was controlled at 28° C. The aeration was 10 LPM and the vessel pressure was maintained at atmospheric pressure. The dissolved oxygen was maintained above 30% by controlling agitation rate. When the culture reached $A_{550}=5$, a continuous 50%(w/w) glucose feed was initiated at a rate of 0.7 ml/min. When the culture reached $A_{550}=3.5$ it was increased to 3.5 ml/min. When the culture achieved $A_{550}=10$ a continuous yeast extract feed (20% w/v) was started at a rate of 0.35 ml/min and continued for the duration of the fermentation. A 50 g/L bolus addition of glucose was added as substrate for the conversion to final product. Additions of Ucon antifoam were added (2 ml/shot) to control foam.

Cell viability was measured by a standard dilution plate count method. An aliquot of culture fluid was diluted serially in a sterile phosphate buffered solution $(NH_4)_2SO_4$, 2.5 g/L; $KH_2PO_4$, 3.0 g/L; $K_2HPO_4$, 2.0 g/L; $MgSO_4 \cdot 7H_2O$, 1.0 g/L. A precise quantity of the diluted culture was spread aseptically on a Luria broth agar plate containing 5 μg/ml tetracycline. After incubation at 30° C. for 24 to 48 hours, the individual colonies were counted. Multiplying the colony count by the known dilution factor gave the number of viable cells per unit volume in the fermentation. The culture was assayed for the presence of 2,5-DKG reductase as described in B.2 above. Total product concentration reflects the amount of 2-KLG and L-idonate.

The results of these fermentations are shown in the table below. The culture containing the controllable expression vector, p269, produced less 2,5-DKG reductase than the culture containing the uncontrollable expression vector ptrpl.35. However, *Erwinia herbicola*/p269 reduced more 2,5-DKG via the 2,5-DKG reductase pathway than *Erwinia herbicola*/ptrpl.35. This unexpected result may be due to the increased viability exhibited by *Erwinia herbicola*/p269. Thus the ability to attenuate the intracellular 2,5-DKG reductase concentration may prevent energy starvation by allowing the minimal energy required for cell viability to flow into cellular metabolism.

| Organism | Age of Measurement Hr | Viability CFU/ml | Relative 2,5-DKG Reductase Activity | Total Product Concentration g/L |
|---|---|---|---|---|
| E. h./pBR322 | 48 | 0.4 × 10⁹ | <1 | <0.1 |
| E. h./ptrpl-35 | 48 | 0.03 × 10⁹ | 16 | 33 |
| E. h./p269 | 48 | 1.0 × 10⁹ | 3 | 45 |

Additional experiments were carried out modulating the expression level by sequential increases in IPTG to induce the tac promoters.

As shown in the table below, increased expression resulted in increased DKG reductase activity and 2-KLG productivity.

In the table below, IPTG is the concentration of isopropylthio-β-galactoside added to the culture medium. Enzyme activity is the sum of the activities of 2,5-DKG reductase and 2-keto aldonate reductase per mg of protein (measured using the Bradford assay, supra). 2-KLG is measured on gram per gram dry cell weight per hour. Finally, the 2-KLG and idonate is measured on a fractional weight basis relative to 2,5-DKG.

| [IPTG] mM | Enzyme Activity umole/mg-P-min | 2-KLG Prod. Rate g/g-DCW-Hr | 2-KLG + IA/DKG |
|---|---|---|---|
| 0.001 | 0.029 | 0.000 | 0.000 |
| 0.005 | 0.051 | 0.004 | 0.025 |
| 0.050 | 0.100 | 0.062 | 0.350 |
| 0.500 | 0.140 | 0.126 | 0.530 |

The results of these experiments establish that flux through a metabolic pathway can be optimized using an inducible promoter, tacII, and lac repressor by adding exogenous inducer to the medium.

EXAMPLE 7

Cloning of the tkrA Gene in *E. herbicola*

A Sau 3A partial digest of *E. herbicola* (ATCC 21998) DNA was ligated into Bam site of pBR322, and this was used to transform MM294 cells to create an Erwinia genomic library. The library was plated onto LB plates containing 50 μg/ml carbenicillin, then the resultant colonies (approx. $10^4$) lifted onto nitrocellulose filters. Filters were then overlaid, colony side up, onto MacConkey plates containing 1.0% 2-KDG plus 50 γ/ml carbenicillin. One red colony was picked and restreaked onto a minimal M9 plate containing 0.2% 2-KDG, 50 γ/ml carbenicillin, and 12.5 μg/ml thiamine. A plasmid was isolated from these cells using standard procedures and was shown to be pBR322 with a 9.5 kb insert in the Bam site; this was termed p370. This plasmid was digested with the restriction enzymes SalI. SohI, EcoRI, and HindIII, the various resultant fragments subcloned into pBR322, and the subclones tested on MacConkey/2-KDG and 2-KDG minimal plates, as described above (FIG. 3). One subclone (p460) contained a 2.2 kb EcoRI/SohI (partial) fragment of Erwinia DNA and scored positive in the screens. Another subclone (p393) contained a 4.0 kb SalI/EcoRI fragment of *E. herbicola* DNA and was also positive in the screens. The DNA sequence of the 2.2kb region between the SphI and the EcoRI sites was determined and the 2-keto reductase gene found by aligning the translated DNA sequence with N-terminal amino acid sequence from the purified reductase (FIG. 4).

EXAMPLE 8

Deletion of the tkrA Chromosomal Gene in *E. herbicola*

Plasmid p393 contains the entire tkrA gene and allows growth of *E. coli* strain 294 on 2-KDG as the sole source of carbon. A unique sac II site was cleaved and the 340 dinucleotide CG was removed from each strand using Klenow DNA polymerase. The resulting plasmid having blunt ends was ligated with T4 DNA ligase, cleaved again with sac II, and then transformed into strain MM294 on rich media plates. The resulting transformants were screened on minimal 2-KDG as sole source of carbon. One such clone was designated p393Δ3. DNA sequence analysis of this clone indicated that, as expected, a 2 nucleotide pair deletion had occurred causing a frameshift which caused translation metabolic pathways, but by their specific deletion as well.

EXAMPLE 12

Cloning of tkrB from *Erwinia herbicola*

Genomic DNA from the Erwinia herbicola (ATCC 21998) tkrA3 strain (see above) was partially digested with Sau3A and fragments 2–10 kb in length cloned into the BamHI site of plasmid pBR322, as described above in Example 7 for the tkrA gene cloning. This library (ca. 10^4 independent clones) was plated onto minimal (M9) plates containing 0.2% 2-KDG, 50 μg/ml carbenicillin, and 12.5 μg thiamine. "Miniprep" DNA was prepared from clones that grew on this medium and screened by means of a HincII restriction digest. From one class of clones, all with a restriction fragment in the insert in common that was not present in the tkrA gene, one clone (p665) was chosen for further analysis. Restriction fragments of p665 were subcloned into pBR322 and analyzed for their ability to support the growth of *E. coli* MM294 cells on minimal 2-KDG media, as described above for tkrA in Example 7. The DNA sequence of a 2.6 kb insert in one of these, plasmid p720, (between the pBR322 BamHI and SphI sites) that contains the tkrB gene is shown in FIG. 11. The identity of the tkrB gene was confirmed by comparing the translated DNA sequence with N-terminal amino acid sequence from purified 2-keto aldonate reductase B.

EXAMPLE 13

Mutagenesis and Regulation of the TkrB Gene

The tkrB gene in the *Erwinia herbicola* tkrAΔ3 strain may be mutagenized by chemical mutagens or radiation, or mutagenized by a combination of in vitro and recombinant methods (as described above for mutagenesis of the tkrA gene), and mutants isolated by screening on appropriate indicator plates or for lack of growth on 2-keto-D-gluconate as a sole carbon source. A method for doing this is described above for tkrA.

Alternatively, if mutagenesis of tkrB is a lethal event, its expression can be put under the control of a promoter that is regulatable in *Erwinia herbicola*. In this way, expression of tkrB can be made dependent on the presence of an exogenous inducer (e.g., lactose or IPTG) or other experimentally controllable condition. A similar approach has been used to control the expression of the signal peptidase gene in *E. coli* (Dalby and Wickner, *J. Biol. Chem.* 260:15925 [1985]). The means by which this can be achieved in *Erwinia herbicola* (ATCC 21998) or mutant strains thereof, or in *A. cerinus* (ATCC 39140) or mutant strains thereof, are detailed below.

Plasmid p720 is digested with BspHI, treated with *E. coli* DNA polymerase I Klenow fragment and the four deoxynucleoside triphosphates to produce blunt ends, digested with BamHI, and the 1.1 kb Bsphi(blunt)-/BamHI fragment, containing the *Erwinia herbicola* tkrB gene, is isolated by agarose gel electrophoresis. Similarly, the plasmid pHGH907 tacIIΔRI5' (De Boer et al.. supra) is digested with EcoRI, treated with the four dNTPs and *E. coli* DNA polymerase I Klenow fragment, digested with BamHI. and the 4.2 kb BamHI/EcoRI (blunt) fragment, containing the pBR322 origin of replication, ampicillin resistance gene, the tacII promoter, and a synthetic ribosome binding site, is isolated. These two fragments are joined by use of T4 DNA ligase to produce plasmid pTKRBtacII, containing the *Erwinia herbicola* tkrB gene under the control of the tacII promoter. This plasmid is then used to transform the lacI$^q$ *E. coli* strain, D1210, which is tested for IPTG-dependent growth on minimal 2-KDG plates, as described above.

The "GenBlock" Kanamycin resistance cartridge (Pharmacia) is digested with HaeII, treated with mung bean exonulease to produce blunt ends, and the 1.5 kb fragment containing the Kanamycin resistance gene isolated. This is inserted into the HincII site of plasmid pUC19 (Yanisch-Perron et al., *Gene* 33:103 [1985]). This plasmid is then digested with XbaI. treated with dNTPs and Klenow fragment to produce blunt ends, and digested with BamHI. Plasmid p720 is digested with Bsphi, treated with Klenow fragment and dNTPs, digested with BamHI and the 1.2 kb BamHI/Bsphi(blunt) fragment, containing *Erwinia herbicola* sequences "upstream" of the tkrB gene, isolated. This fragment is then inserted into the BamHI/XbaI(blunt)-digested pUC19-Kan vector.

Figure 12:
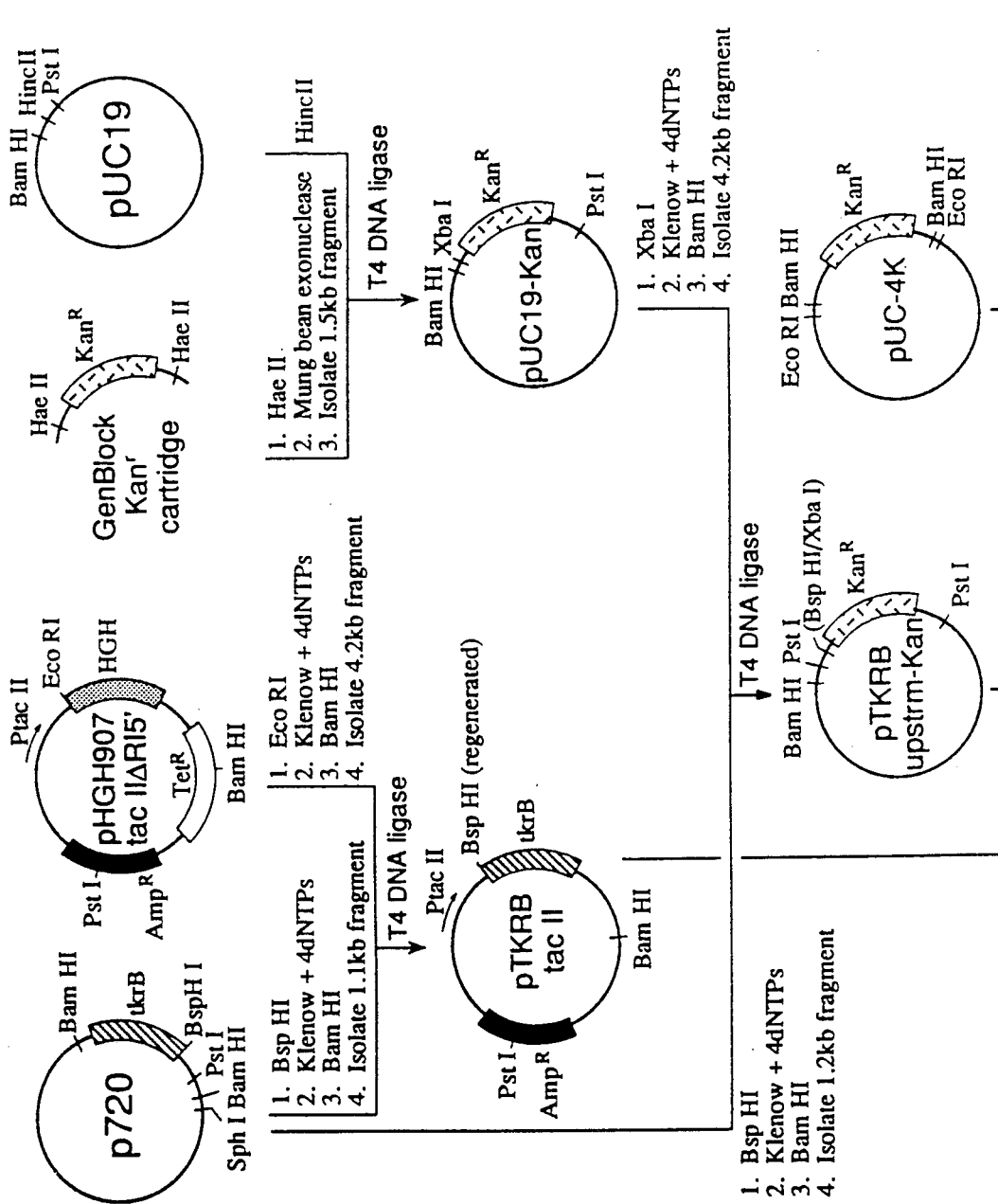
FIG. 12 shows the construction of the vector containing the tkrB gene under control of the tacII promoter.
Figure 12:
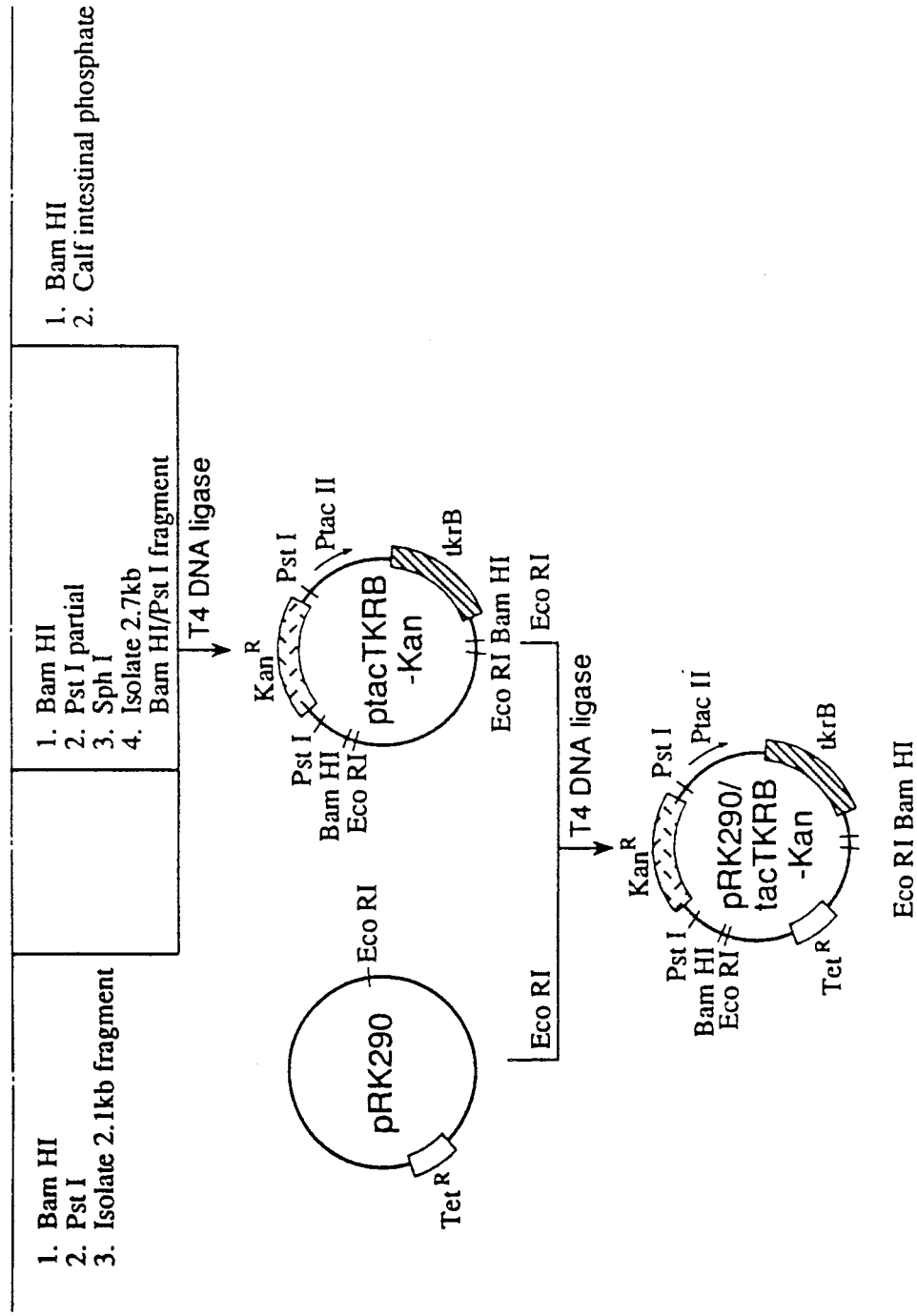

The 2.7 kb fragment containing the kanamycin resistance gene fused to the sequences upstream of the tkrB gene was then excised from the above plasmid via a PstI partial digest and a BamHI digest. The 2.1 kb fragment containing the tkrB gene under the control of the tacII promoter was also isolated via a BamHI/PstI digest from plasmid pTKRBtacII. These two fragments were joined in a 3-way ligation to pUC-4K which was digested with BamHI and treated with calf intestinal phosphatase to prevent intramolecular religation. Colonies containing the correct fragments in the correct orientation are identified by hybridization to specific probes and by restriction analysis. One such resultant plasmid, ptacTKRB-Kan, contains the tkrB "upstream" sequences, the Kanamycin resistance marker, and the tkrB gene under the control of the tacII promoter, all fused in that order and contained on a single 4.8 kb EcoRI fragment (FIG. 12).

In order to incorporate this construct into the *Erwinia herbicola* chromosome in place of the endogenous tkrB control sequences, the method of Ruvkun and Ausubel (*Nature* 289:85 [1981]) is used. Briefly, the 4.8 kb EcoRI fragment from plasmid ptacTKRB-Kan is cloned into the EcoRI site of plasmid pRK290, then this is used to transform *Erwinia herbicola* (ATCC 21998) or mutants thereof (e.g., tkrA3). After co-transformation with plasmid pR751 and simultaneous selection for trimethoprim and kanamycin, the incompatibility of these two plasmids forces integration of the Kan$^R$-tacII-tkrB sequences, via homologous recombination, into the site of the tkrB gene in the host chromosome. See FIG. 13. After providing, in trans, an *E. coli* lac repressor function (conveniently expressed on an autonomously replicating plasmid—see example 6 above) the tkrB gene expression can be regulated by an exogenous to be optimized during both growth and production phases. Moreover, this approach is generally applicable to other 2,5-DKG producing cells such as *A. cerinus* with only minor modifications (e.g., use of conjugation rather than transformation for introduction of the plasmid DNA into the cells. See U.S. patent application Ser. No. 07/053,290).

We claim:

1. A process for converting glucose to 2-keto-L-gulonic acid (2-KLG) comprising culturing in a medium containing said glucose under suitable metabolic conditions, 2,5-diketo-D-gluconic acid (2,5-DKG) producing bacterial cells to which genetic material was transferred wherein the transfer of said genetic material renders the cells capable of converting said 2,5-DKG into 2-KLG comprising a) identifying L-idonic acid (IA) and 5-keto-D-gluconate (5-KDG) as secondary metabolites and the corresponding secondary metabolic pathways, and the 2-ketoaldonate reductase (2-KR) enzymes catalyzing the conversions resulting in the metabolic diversion of 2-KLG to IA and 2,5-DKG to 5-KDG, and b) eliminating said metabolic diversion by blocking at least one of the identified secondary metabolites, secondary metabolic pathways, and enzymes.

2. The process of claim 1 wherein said elimination is performed by mutagenesis.

3. The process of claim 1 wherein in order to transfer said genetic material, an expression vector encoding a 2,5-DKG reductase enzyme was transferred into said 2,5-DKG producing bacterial cells.

4. The process of claim 1 wherein the secondary metabolite blocked is L-idonic acid.

5. The process of claim 1 wherein the secondary metabolic pathway blocked comprises the reduction of 2-KLG to L-idonic acid.

6. The process of claim 1 wherein the transfer of genetic material was by an expression vector comprising an inducible promoter.

7. The process of claim 6 wherein the inducible promoter is a tacII promoter.

8. The process of claim 1 wherein the 2,5-DKG producing bacterial cells to which genetic material was transferred are of the genus Erwinia.

9. The process of claim 8 wherein said bacterial cells are those of an *Erwinia herbicola* strain.

10. The process of claim 1 wherein the 2,5-DKG producing bacterial cells to which genetic material was transferred are of the genus Acetobacter.

11. The process of claim 10 wherein said bacterial cells are those of an *Acetobacter cerinus* strain.

12. A process for converting glucose to 2-KLG by culturing in a medium containing said glucose under suitable metabolic conditions, cells of bacterial strains selected from the group consisting of *Acetobacter cerinus* and *Erwinia herbicola* to which genetic material encoding a 2,5-DKG reductase enzyme was transferred, comprising eliminating the metabolic diversion of 2-KLG to IA or of 2,5-DKG to 5-KDG by blocking at least one of the secondary metabolites, secondary metabolic pathways and 2-KR enzymes resulting in said metabolic diversion.

* * * * *